United States Patent [19]

Kasica et al.

[11] Patent Number: 5,830,884
[45] Date of Patent: Nov. 3, 1998

[54] PHARMACEUTICAL PRODUCTS CONTAINING THERMALLY-INHIBITED STARCHES

[75] Inventors: James J. Kasica, Whitehouse Station, N.J.; David J. Thomas, Eagan, Minn.; James P. Zallie, Hillsborough, N.J.

[73] Assignee: National Starch and Chemical Investment Holding Corporation, Wilmington, Del.

[21] Appl. No.: 595,008

[22] Filed: Jan. 31, 1996

Related U.S. Application Data

[63] Continuation-in-part of Ser. No. 375,321, Jan. 18, 1995, abandoned.

[30] Foreign Application Priority Data

Jan. 17, 1996 [WO] WIPO .................... PCT/US96/00612

[51] Int. Cl.$^6$ ............................................... C09J 103/02
[52] U.S. Cl. ....................................... 514/160; 514/206.1
[58] Field of Search ............................ 106/206.1; 514/60

[56] References Cited

U.S. PATENT DOCUMENTS

| | | | |
|---|---|---|---|
| 2,274,789 | 3/1942 | Horesi | 127/38 |
| 2,317,752 | 4/1943 | Fuller | 127/33 |
| 2,373,016 | 4/1945 | Daly et al. | 127/70 |
| 2,427,328 | 9/1947 | Schopmeyer et al. | 127/32 |
| 2,590,912 | 4/1952 | Yarber | 127/32 |
| 2,661,349 | 2/1953 | Caldwell et al. | 260/224 |
| 2,791,512 | 5/1957 | Hatch et al. | 106/208 |
| 2,897,086 | 7/1959 | Sowell et al. | 99/139 |
| 2,938,901 | 5/1960 | Kerr et al. | 260/233.5 |
| 2,951,776 | 9/1960 | Scallet et al. | 127/71 |
| 3,034,911 | 5/1962 | McKee et al. | 106/210 |

(List continued on next page.)

FOREIGN PATENT DOCUMENTS

| | | |
|---|---|---|
| 1 150 934 | of 0000 | Canada . |
| 2 013 133 | 10/1990 | Canada . |
| 0 129 227 A1 | 12/1984 | European Pat. Off. . |
| 0 257 338 A2 | 3/1988 | European Pat. Off. . |
| 0 321 216 A2 | 6/1989 | European Pat. Off. . |
| 0 415 385 A2 | 3/1991 | European Pat. Off. . |
| 0 490 424 A1 | 6/1992 | European Pat. Off. . |
| 60-97331 | of 0000 | Japan . |
| 61-254602 | 11/1986 | Japan . |
| 63/194725 | 9/1989 | Japan . |
| 1224281 | 3/0000 | United Kingdom . |
| 263897 | 12/1926 | United Kingdom . |
| 530226 | 12/1940 | United Kingdom . |
| 595552 | 12/1947 | United Kingdom . |
| 1479515 | 7/1977 | United Kingdom . |
| WO 80/02374 | 11/1980 | WIPO . |
| WO 95/04082 | 2/1995 | WIPO . |

OTHER PUBLICATIONS

J.W. Donovan et al., *Cereal Chemistry*, "Differential Scanning Calorimetry of Heat–Moisture Treated Wheat and Potato Starches", vol. 60, No. 5, pp. 381–387 (1983).

Cristina Ferrero et al., *Journal of Food Processing and Preservation*, "Stability of Frozen Starch Pastes: Effect of Freezing, Storage and Xanthan Gum Addition", vol. 17, pp. 191–211 (1993).

Jyrki Heinämäki et al., *International Journal of Pharmaceutics*, "Formulations Releasing the Drug Proximal to the Pylorus in the Dog", vol. 48, pp. 41–61 (1988)—see p. 10, lines 17–20.

Dong–Hyun Lee et al., *Chem. Eng. Technol.*, "Drying Characteristics of Starch in an Inert Medium Fluidized Bed", vol. 16, pp. 263–269 (1993).

Vincent Lenaerts et al., *Journal of Controlled Release*, "Controlled Release of Theophylline From Cross–linked Amylose Tablets", vol. 15, pp. 39–46 (1991)—see p. 10, line 20–23.

Irving Martin, *Journal of Applied Polymer Science*, "Crosslinking of Starch by Alkaline Roasting", vol. 11, No. 5, pp. 1283–1288 (May 1967).

Masaaki Mori et al., *Jounal of Pharmaceutical Sciences*, "Prolongation of Antipyretic Action and Reduction of Gastric Ulcerogenicity in the Rat by Controlled–Release Granules of Bermoprofen, A New Nonsteriodal Anti–Inflammatory Drug", vol. 80, No. 9, pp. 876–880, (Sep. 1991)—see p. 10, lines 24–27.

L. Sair et al., *Industrial and Engineering Chemistry*, "Water Sorption by Starches", vol. 36 No. 3, pp. 205–208.

Rolf Stute, *Starch/Stärke*, "Hydrothermal Modification of Starches: The Difference between Annealing and Heat/Moisture–Treatment", vol. 44, No. 6, pp. 205–214 (1992).

"The bepex Fluid Bed" (Bulletin).

Copy of PCT Search Reports for PCT/US95/00682, PCT/US95/00688, PCT/US95/00684, PCT/US94/08559, and PCT/US95/09138.

Smelik et al., "Process for Manufacture of Starch with Reduced Gluten Content", C.A. Abstract 108, No. 20 169546S (1988).

P.H. List et al., "Hagers Handbuch der Pharmazeutischen Praxis", 1977.

"Handbook of Pharmaceutical Excipients", 1986.

Ullmanns Encyclopädie der technischen Chemie, vol. 22, 1982.

Copy of PCT Search Reports for PCT/US96/00612, PCT/US96/00999, PCT/US96/00613, PCT/US96/07076, PCT/US96/00629, and PCT/US96/07071.

Copy of PCT Search Report for PCT/US96/00988.

WPIDS Abstract AN 95–082188, corresponding to WO 9504082, Chiu et al., 1995.

*Primary Examiner*—Keith D. MacMillan
*Attorney, Agent, or Firm*—Margaret B. Kelley

[57] ABSTRACT

Thermally-inhibited starches and flours are used in pharmaceutical products as a diluent, filler, carrier, binder, disintegrant, coating, thickener, moisture sink, and the like. The starches and flours are inhibited by dehydrating the starch or flour to substantially anhydrous or anhydrous and then heat treating the anhydrous or substantially anhydrous starch or flour for a time and at a temperature sufficient to inhibit the starch or flour. The dehydration can be carried out by heating the starch or flour, by extracting the starch or flour with a solvent, or by freeze drying. Preferably, the pH is adjusted to a neutral pH or above prior to the dehydration and heat treatment.

22 Claims, No Drawings

U.S. PATENT DOCUMENTS

| | | | |
|---|---|---|---|
| 3,035,045 | 5/1962 | Trimnell et al. | 260/233.3 |
| 3,155,527 | 11/1964 | Mentzer | 106/210 |
| 3,331,697 | 7/1967 | Salmon | 106/213 |
| 3,399,081 | 8/1968 | Bernetti et al. | 127/71 |
| 3,408,214 | 10/1968 | Mentzer | 106/212 |
| 3,453,368 | 7/1969 | Magid | 424/280 |
| 3,463,668 | 8/1969 | Evans et al. | 127/32 |
| 3,477,903 | 11/1969 | Semegran et al. | 161/266 |
| 3,490,742 | 1/1970 | Nichols et al. | 252/99 |
| 3,490,917 | 1/1970 | Doe et al. | 99/93 |
| 3,515,591 | 6/1970 | Feldman et al. | 127/32 |
| 3,563,798 | 2/1971 | Germino et al. | 127/32 |
| 3,578,497 | 5/1971 | Hjermstad | 127/32 |
| 3,607,394 | 9/1971 | Germino et al. | 127/32 |
| 3,607,396 | 9/1971 | Germino et al. | 127/71 |
| 3,622,677 | 11/1971 | Short et al. | 424/361 |
| 3,640,756 | 2/1972 | Beersma et al. | 117/76 |
| 3,690,938 | 9/1972 | Swift | 117/122 |
| 3,725,387 | 4/1973 | McClendon et al. | 260/233.3 |
| 3,810,783 | 5/1974 | Bomball | 117/122 |
| 3,844,807 | 10/1974 | Bramel | 106/213 |
| 3,949,104 | 4/1976 | Cheng et al. | 426/578 |
| 3,950,593 | 4/1976 | Bomball | 428/476 |
| 3,967,975 | 7/1976 | Idaszak | 127/23 |
| 3,977,897 | 8/1976 | Wurzburg et al. | 127/71 |
| 4,013,799 | 3/1977 | Smalligan et al. | 426/578 |
| 4,026,986 | 5/1977 | Christen et al. | 264/301 |
| 4,072,535 | 2/1978 | Short et al. | 106/210 |
| 4,131,574 | 12/1978 | Isherwood et al. | 260/17.3 |
| 4,256,509 | 3/1981 | Tuschhoff et al. | 127/32 |
| 4,266,348 | 5/1981 | Ledding | 34/10 |
| 4,280,851 | 7/1981 | Pitchon et al. | 127/33 |
| 4,303,451 | 12/1981 | Seidel et al. | 127/32 |
| 4,303,452 | 12/1981 | Ohira et al. | 127/32 |
| 4,308,251 | 12/1981 | Dunn et al. | 424/19 |
| 4,329,181 | 5/1982 | Chiu et al. | 106/213 |
| 4,366,275 | 12/1982 | Silano et al. | 524/47 |
| 4,369,308 | 1/1983 | Trubiano | 536/106 |
| 4,383,111 | 5/1983 | Takeo et al. | 536/102 |
| 4,391,836 | 7/1983 | Chiu | 426/578 |
| 4,428,972 | 1/1984 | Wurzburg et al. | 426/578 |
| 4,465,702 | 8/1984 | Eastman et al. | 426/578 |
| 4,491,483 | 1/1985 | Dudacek et al. | 127/33 |
| 4,551,177 | 11/1985 | Trubiano et al. | 106/210 |
| 4,575,395 | 3/1986 | Rudin | 127/32 |
| 4,600,472 | 7/1986 | Pitchon et al. | 159/4.4 |
| 4,610,760 | 9/1986 | Kirkpatrick et al. | 159/4.01 |
| 4,668,692 | 5/1987 | Noorlander et al. | 514/390 |
| 4,728,512 | 3/1988 | Mehta et al. | 424/458 |
| 4,798,724 | 1/1989 | Khanna et al. | 424/480 |
| 4,818,542 | 4/1989 | DeLuca et al. | 424/491 |
| 4,847,371 | 7/1989 | Schara et al. | 536/111 |
| 4,888,178 | 12/1989 | Rotini et al. | 424/468 |
| 4,904,476 | 2/1990 | Mehta et al. | 424/456 |
| 5,004,614 | 4/1991 | Staniforth | 424/466 |
| 5,037,929 | 8/1991 | Rajagopalan et al. | 426/578 |
| 5,085,228 | 2/1992 | Mooney et al. | 131/37 |
| 5,087,649 | 2/1992 | Wegner et al. | 524/30 |
| 5,149,799 | 9/1992 | Rubens | 536/102 |
| 5,155,140 | 10/1992 | Marten et al. | 523/100 |
| 5,181,959 | 1/1993 | Nagai et al. | 106/211 |
| 5,292,519 | 3/1994 | Mauro et al. | 424/465 |
| 5,329,004 | 7/1994 | Eden et al. | 536/109 |
| 5,368,690 | 11/1994 | Solarek et al. | 162/175 |

PHARMACEUTICAL PRODUCTS CONTAINING THERMALLY-INHIBITED STARCHES

This application is a continuation-in-part of prior pending PCT application (Ser. No. to be assigned) filed Jan. 17, 1996 and prior pending U.S. application Ser. No. 08/375,321 filed Jan. 18, 1995 now abandoned.

BACKGROUND OF THE INVENTION

This invention relates to pharmaceutical products containing starches and flours.

Heat Treatment of Starches and Flours

Heat/moisture treatment and annealing of starches and/or flours are taught in the literature and distinguished by the amount of water present. "Annealing" involves slurrying a granular starch with excess water at temperatures below the starch's gelatinization temperature, whereas "heat/moisture-treatment" involves a semi-dry treatment at temperatures below the starch's gelatinization temperature, with no added moisture and with the only moisture present being that normally present in a starch granule (which is typically 10% or more).

In the following discussion, a history of the various heat/moisture and annealing treatments of starch and/or flour is set out.

GB 263,897 (accepted Dec. 24, 1926) discloses an improvement in the heat treatment process of GB 228,829. The process of the '829 patent involves dry heating flour or wheat to a point at which substantially all of the gluten is rendered non-retainable in a washing test and then blending the treated flour or wheat with untreated flour or wheat to provide a blend having superior strength. The improvement of the '897 patent is continuing the dry heating, without, however, gelatinizing the starch, for a considerable time beyond that necessary to render all of the gluten non-retainable. "Dry-heating" excludes heating in a steam atmosphere or an atmosphere containing considerable quantities of water vapor which would tend to gelatinize the starch. The wheat or flour may contain the usual amount of moisture, preferably not greater than 15%. The heat treatment may exceed 7 hours at 77°–93° C. (170°–200° F.), e.g., 8 to 14 hours at 82° C. (180° F.) or 6 hours at 100° C. (212° F.).

GB 530,226 (accepted Dec. 6, 1940) discloses a method for drying a starch cake containing about 40–50% water with hot air or another gas at 149° C. (300° F.) or above without gelatinizing the starch. The starch cake is disintegrated by milling it to a finely divided state prior to drying.

GB-595,552 (accepted Dec. 9, 1947) discloses treatment of starch, more particularly a corn starch, which involves drying the starch to a relatively low moisture content of 1–2%, not exceeding 3%, and subsequently dry heating the substantially moisture-free starch at 115°–126° C. for 1 to 3 hours. The treatment is intended to render the starch free from thermophilic bacteria. The starch should not be heated longer than necessary to effect the desired sterilization.

U.S. Pat. No. 3,490,917 (issued Jan. 20, 1970 to C.A.F. Doe et al.) discloses a process for preparing a non-chlorinated cake flour suitable for use in cakes and sponges having a high sugar to flour ratio. The starch or a flour in which the gluten is substantially or completely detached from the starch granules is heated to a temperature of from 100°–140° C. and then cooled. The conditions are selected so that dextrinization does not occur, e.g., about 15 minutes at 100°–115° C. and no hold and rapid cooling at the higher temperatures. The heat treatment should be carried out under conditions which allow the water vapor to escape. The reduction in moisture content due to the heat treatment depends upon the temperature employed. At treatment temperatures of 100°–105° C., the moisture content is reduced from 10–12% to 8–9%, by weight, while at medium and high temperatures the moisture content is typically reduced to 7% or less. Preferably, during cooling the moisture is allowed to reach moisture equilibrium with the atmosphere. The gelatinization temperature of the heat treated starch or flour is approximately 0.5°–1° C. higher than that of a comparable chlorinated flour or starch. The heating can be carried out in many ways, including heating in a hot air fluidized bed.

U.S. Pat. No. 3,578,497 (issued May 11, 1971 to E. T. Hjermstad) discloses a process for non-chemically improving the paste and gel properties of potato starch and imparting a swelling temperature as much as 20° to 30° F. higher. A concentrated suspension (20–40% dry solids) at a neutral pH (5.5–8.0, preferably 6–7.5) is heated either for a long time at a relatively low temperature or for a short time at successively higher temperatures. The suspension is first heated at a temperature below the incipient swelling temperature of the particular batch of starch being treated (preferably 49° C.–120° F.). Then the temperature is gradually raised until a temperature well above the original swelling temperature is attained. It is essential that swelling be avoided during the different heating periods so that gelatinization does not occur. After this steeping treatment the starch has a higher degree of granular stability. It resists rapid gelatinization and produces a rising or fairly flat viscosity curve on cooling. The pastes are very short textured, non-gumming, non-slimy, cloudy and non-cohesive. They form firm gels on cooling and aging.

U.S. Pat. No. 3,977,897 (issued Aug. 31, 1976 to Wurzburg et al.) discloses a method for preparing non-chemically inhibited amylose-containing starches. Both cereal and root starches can be inhibited, but the inhibition effects are more observable with root starches. Amylose-free starches, such as waxy corn starch, show no or very slight inhibition. The Brabender viscosity of cooked pastes derived from the treated starch was used to determine the inhibition level. Inhibition was indicated by a delayed peak time in the case of the treated corn starch, by the lack of a peak and a higher final viscosity in the case of the treated achira starch, and by the loss of cohesiveness in the case of the treated tapioca starch. The granular starch is suspended in water in the presence of salts which raise the starch's gelatinization temperature so that the suspension may be heated to high temperatures without causing the starch granules to swell and rupture yielding a gelatinized product. The preferred salts are sodium, ammonium, magnesium or potassium sulfate; sodium, potassium or ammonium chloride; and sodium, potassium or ammonium phosphate. About 10–60 parts of salt are used per 100 parts by weight of starch. Preferably, about 110 to 220 parts of water are used per 100 parts by weight of starch. The suspension is heated at 50°–100° C., preferably 60°–90° C., for about 0.5 to 30 hours. The pH of the suspension is maintained at about 3–9, preferably 4–7. Highly alkaline systems, i.e., pH levels above 9 retard inhibition.

U.S. Pat. No. 4,013,799 (issued Mar. 22, 1977, to Smalligan et al.) discloses heating a tapioca starch above its gelatinization temperature with insufficient moisture (15 to 35% by total weight) to produce gelatinization. The starch is heated to 70°–130° C. for 1 to 72 hours. The starch is used as a thickener in wet, pre-cooked baby foods having a pH below about 4.5.

U.S. Pat. No. 4,303,451 (issued Dec. 1, 1981 to Seidel et al.) discloses a method for preparing a pregelatinized waxy maize starch having improved flavor characteristics reminiscent of a tapioca starch. The starch is heat treated at 120°–200° C. for 15 to 20 minutes. The pregelatinized starch has gel strength and viscosity characteristics suitable for use in pudding mixes.

U.S. Pat. No. 4,303,452 (issued Dec. 1, 1981 to Ohira et al.) discloses smoking a waxy maize starch to improve gel strength and impart a smoky taste. In order to counteract the smoke's acidity and to obtain a final product with a pH of 4–7, the pH of the starch is raised to pH 9–11 before smoking. The preferred water content of the starch during smoking is 10–20%.

The article "Differential Scanning Calorimetry of Heat-Moisture Treated Wheat and Potato Starches" by J. W. Donovan et al. in *Cereal Chemistry*, Vol. 60, No. 5, pp. 381–387 (1983) discloses that the gelatinization temperature of the starches increased as a result of the heat/moisture treatment or annealing. See also the article "A DSC Study Of The Effect Annealing On Gelatinization Behavior Of Corn Starch" by B. R. Krueger et al. in Journal of Food Science, Vol. 52, No. 3, pp. 715–718 (1987).

U.S. Pat. No. 4,391,836 (issued Jul. 5, 1983 to C.-W. Chiu) discloses instant gelling tapioca and potato starches which are non-granular and which have a reduced viscosity. Unmodified potato and tapioca starches do not normally gel. The starches of the patent are rendered non-granular and cold-water-dispersible by forming an aqueous slurry of the native starch at a pH of about 5–12 and then drum-drying the slurry. The starches are rendered gelling by heat treating the drum-dried starch for about 1.5 to 24 hours at 125°–180° C. to reduce the viscosity to within defined Brabender viscosity limitations.

U.S. Pat. No. 4,491,483 (issued Jan. 1, 1985 to W. E. Dudacek et al.) discloses subjecting a semi-moist blend of a granular starch with at least 0.25 wt. % of a fatty acid surfactant and sufficient water (about 10–40 wt. %) to a heat-moisture treatment at from about 50°–120° C., followed by drying to about 5–15 wt. %, preferably 10 wt. %, moisture. The heat-moisture treated starch-surfactant product is characterized by a hot water dispersibility of from about 60–100% and a higher pasting temperature than the granular starch from which it is derived. Preferably, the treatment takes place in a closed container so that the moisture can be maintained at a constant level. The preferred conditions are 3 to 16 hours at 60°–90° C. Degradation and dextrinization reactions are undesirable as they destroy the thickening ability of the starch. The use of conditions, such as, e.g., 35% moisture at 90° C. for 16 hours results in reduced paste viscosity. It is believed the presence of the surfactant during the treatment permits formation of a complex within the partially swollen starch matrix with straight chain portions of the starch molecules. The limited moisture environment allows complex formation without gelatinization.

Japanese Patent Publication No. 61-254602, (published Dec. 11, 1987) discloses a wet and dry method for heating waxy corn starch and derivatives thereof to impart emulsification properties. The wet or dry starch is heated at 100°–200° C., preferably 130°–150° C., for 0.5 to 6 hours. In the dry method, the water content is 10%, preferably 5%, or less. In the wet method, the water content is 5 to 50%, preferably 20–30%. The pH is 3.5–8, preferably 4–5.

The article "Hydrothermal Modification of Starches: The Difference between Annealing and Heat/Moisture-Treatment", by Rolf Stute, Starch/Stärke Vol. 44, No. 6, pp. 205–214 (1992) reports almost identical modifications in the properties of potato starch with annealing and heat/moisture treatments even through the alteration of the granular structure is different. The Brabender curves of the heat/moisture-treated and annealed potato starches show the same typical changes, including a higher gelatinization temperature and a lower peak viscosity or no peak. The DSC curves also show a shift to higher gelatinization temperatures for both treatments. A combined treatment involving annealing a heat/moisture-treated potato starch leads to a further increase in gelatinization temperature without detectable changes in gelatinization enthalapy and with retention of the viscosity changes caused by the heat treatment. A combined treatment involving annealing a heat/moisture-treat potato starch does not lower the gelatinization temperature, when compared to the base starch, and increases the gelatinization temperature at higher heat/moisture treatment levels.

Chemical Crosslinking of Starches and Flours

Starches and flours are chemically modified with difunctional reagents such as phosphorus oxychloride, sodium trimetaphosphate, mixed adipic/acetic anhydride, and epichlorohydrin to produce chemically crosslinked starches having excellent tolerance to processing variables such as heat, shear, and pH extremes. Such chemically crosslinked starches (also referred to as "inhibited starches") provide a desirable smooth texture and possess viscosity stability throughout processing operations and normal shelf life.

In contrast, when unmodified (i.e., non-crosslinked) starches, particularly waxy-based starches, are gelatinized, they reach a peak viscosity which soon begins to breakdown, lose thickening capacity and textural qualities, and behave unpredictably during storage as a result of the stresses encountered during processing. Heat, shear, and/or an extreme pH, especially an acidic pH, tend to fully disrupt the starch granules and disperse the starch.

Pharmaceutical Products

Starches are used in pharmaceutical products as a filler, diluent, or carrier; as a wet granulation or direct compression binder; as a disintegrant or erosion-promoting agent; as an energy source for absorbed bacteria; in controlled release compositions; in extended-release suspensions; as a dusting powder; as a coating; and for forming capsule shells. See U.S. Pat. No. 2,938,901 (issued May 31, 1960 to R. W. Kerr) which discloses the use of a granular starch crosslinked with sodium trimetaphosphate as a surgical dusting powder; U.S. Pat. No. 3,034,911 (issued May 15, 1962 to I. K. McKee et al.) which discloses the use of a cold water swelling and cold water insoluble starch in intact granular form (e.g., corn phosphate or potato sulfate) as a disintegrant; U.S. Pat. No. 3,453,368 (issued Jul. 1, 1969 to L. Magid) which discloses the use of pregelatinized starches, optionally modified and stabilized, as binders for compressed ascorbic acid tablets; U.S. Pat. No. 3,490,742 (issued Jan. 20, 1970 to G. K. Nichols et al.) which discloses a non-granular amylose (at least 50%) obtained from the fractionation of corn starch for use as a binder-disintegrant in direct compression and dry granulation tablets; U.S. Pat. No. 3,622,677 (issued Nov. 23, 1971 to R. W. P. Short) which discloses the use of a partially cold-water-soluble and cold-water-swelling starch, derived from a compacted granular starch, as a binder-disintegrant; U.S. Pat. No. 4,072,535 (issued Feb. 7, 1978 to R. W. P.

Short) which discloses a precompacted starch having birefringent granules, non-birefringent granules, and some aggregates and fragments for use as a binder-disintegrant; U.S. Pat. No. 4,026,986 (issued May 31, 1977 to J. Duane et al.) which discloses the use of water-soluble starch ethers (e.g., hydroxyalklyl ethers) containing at least 50% amylose for use in forming capsule shells; U.S. Pat. No. 4,308,251 (issued Dec. 29, 1981 to J. M. Dunn et al.) which discloses the use of corn, rice, potato, and modified starches as an erosion-promoting agent in controlled release formulations prepared by wet granulation; U.S. Pat. No. 4,369,308 (issued Jan. 18, 1983 to P. C. Trubiano) which discloses the use of crosslinked pregelatinized starches as tablet disintegrants; U.S. Pat. No. 4,383,111 (issued May 10, 1983 to K. Takeo et al.) which discloses a substantially non-birefringent starch which retains its shell film structure for use as a disintegrant; U.S. Pat. No. 4,551,177 (issued Nov. 5, 1985 to P. C. Trubiano et al.) which discloses the use of acid- and/or alpha-amylase-converted starches as tablet binders; U.S. Pat. No. 4,668,692 (issued May 26, 1987 to D. O. Noorlander et al.) which disclose the use of corn starch as a carrier for dry powdered germicides and healing compositions; U.S. Pat. No. 4,728,512 and U.S. Pat. No. 4,904,476 (issued Mar. 1, 1988 and Feb. 27, 1990 to A. M. Mehta et al.) which discloses the use of sodium starch glycolate (i.e., the sodium salt of a carboxymethyl starch ether) as a disintegrant in an undercoating for the 3rd of three groups of spheroids having different controlled release characteristics contained in a gelatin capsule and which also discloses the use of starch as an excipient in the group of double coated spheroids; U.S. Pat. No. 4,818,542 which discloses starch as a biodegradable or bioerodable polymer for porous micropheres possibly coated with a crosslinking agent to inhibit or control drug release; U.S. Pat. No. 4,888,178 (issued Dec. 19, 1989 to L. G. Rotini et al.) which discloses the use of starch, preferably maize starch, and sodium starch glycolate as disintegrants in the immediate release of a programmed release Naproxen formulation containing immediate release and controlled release granulates in the form of tablets, capsules, or suspensions in a suitable liquid media; U.S. Pat. No. 5,004,614 (issued Apr. 2, 1991 to J. N. Staniforth) which discloses the use of starches as pharmaceutical fillers in controlled release devices containing an active agent and a release agent and the use of crosslinked sodium or uncrosslinked carboxymethyl starch for the coating; U.S. Pat. No. 5,292,519 (issued Mar. 8, 1994 to D. J. Mauro et al.) which discloses the use of a white corn starch (obtained from a starch bearing plant which is homozygous with the white gene) as a binder.

See also Canadian Patent Application 2,013,133 which discloses the use of hydrocolloids such as corn or potato starch, as well as modified or pregelatinized starches, as disintegrants in fat-free rectal or vaginal pharmaceutical capsules or as the hard casing of capsules; WO 80/02374 which discloses the use of hydroxyalkyl starches in controlled release formulations.

Further see the articles, by J. Heinamaki et al. in Intl. J. Pharm. 48, 51–61 (1988) which disclose the use of pregelatinized starches as disintegrants in coated sustained-release tablets; by V. Lenaerts et al. in J. Controlled Release 15, 39–46 (1991) which discloses the use of amylose crosslinked with epichlorohydrin as a matrix for controlled release drugs (e.g., theophylline); and by M. Mori et al. in J. Pharm. Sci. 80 (a) 876–880 (September 1991) which discloses the use of corn starch as a diluent in sustained release granules which contain both immediate release and slow release granules.

Regulatory acceptance is an important consideration in selecting pharmaceutical ingredients. There is a need for starches and flours which are inert, low in moisture content, and functional and which can provide a clean label declaration. Thus, there is a need for chemically unmodified starches or flours for use in pharmaceuticals.

SUMMARY OF THE INVENTION

The present invention provides improved pharmaceutical products such as tablets, liquid medicaments, dusting powders, suppositories, and the like which contain an active ingredient and a thermally-inhibited starch or flour as a filler, diluent, carrier, viscosifier, wet granulation or direct compression binder, disintegrant, coating, moisture sink, and like uses where starches are conventionally used.

As used herein, "active ingredient" means an ingredient which provides the desired pharmaceutical effect, i.e., therapeutic, preventative, nutritive, and the like.

The starches and flours are thermally inhibited, without the addition of chemical reagents, in a heat treatment process that results in the starch or flour becoming and remaining inhibited. The starches and flours are referred to as "inhibited" or "thermally-inhibited (abbreviated "T-I"). When these thermally-inhibited starches and flours are dispersed and/or cooked in water, they exhibit the textural and viscosity properties characteristic of a chemically-crosslinked starch. The starch granules are more resistant to viscosity breakdown. This resistance to breakdown results in what is subjectively considered a non-cohesive or "short" textured paste, meaning that the gelatinized starch or flour tends to be salve-like and heavy in viscosity rather than runny or gummy.

When the thermally-inhibited starches and flours are non-pregelatinized granular starches or flours, the starches or flours exhibit an unchanged or reduced gelatinization temperature. In contrast, most annealed and heat/moisture treated starches show an increased gelatinization temperature. Chemically-crosslinked starches show an unchanged gelatinization temperature. It is believed the overall granular structure of the thermally-inhibited starches and flours has been altered.

The starches and flours that are substantially completely thermally inhibited will resist gelatinization. The starches and flours that are highly inhibited will gelatinize to a limited extent and show a continuing rise in viscosity but will not attain a peak viscosity. The starches and flours that are moderately inhibited will exhibit a lower peak viscosity and a lower percentage breakdown in viscosity compared to the same starch that is not inhibited. The starches and flours that are lightly inhibited will show a slight increase in peak viscosity and a lower percentage breakdown in viscosity compared to the same starch that is not inhibited.

The starches and flours are inhibited by a process which comprises the steps of dehydrating the starch or flour until it is anhydrous or substantially anhydrous and then heat treating the anhydrous or substantially anhydrous starch or flour at a temperature and for a period of time sufficient to inhibit the starch or flour. As used herein, "substantially anhydrous" means containing less than 1% moisture by weight. The dehydration may be a thermal dehydration or a non-thermal dehydration such alcohol extraction or freeze drying. An optional, but preferred, step is adjusting the pH of the starch or flour to neutral or greater prior to the dehydration step.

The amount of thermal inhibition required will depend on the reason the starch or flour is included in the pharmaceutical product, e.g., for thickening or gelling or as a moisture sink, as well as the particular processing conditions used to prepare the pharmaceutical product. Pharmaceuticals prepared with the thermally-inhibited starches and flours will possess viscosity stability, process tolerance such as resistance to heat, acid and shear, and improved texture.

Depending on the extent of the heat treatment, various levels of inhibition can be achieved. For example, lightly inhibited, higher viscosity products with little breakdown, as well as highly inhibited, low viscosity products with no breakdown can be prepared by the thermal inhibition processes described herein.

For use as wet granulation binders any physical form (non-pregelatinized granular form or pregelatinized granular or non-granular form) of the thermally-inhibited starches or flours can be used. For use as direct compression binders, the preferred forms are non-pregelatinized granular starches or pregelatinized granular starches. For disintegrants, fillers, diluents, carriers, dusting powders, coatings, and moisture sinks, all physical forms of the thermally-inhibited starches and flours are suitable.

The pregelatinized starches and flours are prepared using conventional methods which disrupt or retain the granular structure.

Where white powders are desired, usually with dry powder applications, the thermally-inhibited starch or flour is bleached using known bleaching agents.

The bleaching agents useful herein include chlorite salts/ such as sodium chlorite; hypochlorite salts/such as calcium or sodium hypochlorite; peroxides/such as hydrogen peroxide or peracetic acid; persulfate salts/such as sodium, potassium or ammonium persulfate; permanganate salts/such as potassium permanganate; chlorine dioxide; and ozone. These bleaching agents are well known in the art.

Thermally-inhibited starches and flours are used where a low moisture content and/or improved flowability are required, e.g., dry powder uses. Their substantially reduced microbial content makes them advantageous for all pharmaceutical applications. When the thermally-inhibited starches and flours are subsequently handled, whether for pH adjustment, additional physical modification or chemical modification (e.g., bleaching), or stored, the low moisture content, improved flowability and substantially reduced microbial content may be compromised. One skilled in the art will recognize that the thermally-inhibited starches and flours have to be carefully handled to maintain, or if necessary, re-establish these beneficial properties.

For some applications, chemical modifications of the thermally-inhibited starches and flours are not desirable as there may be an interaction with the active ingredient in the pharmaceutical. The thermally-inhibited starches and flours are advantageous as a replacement for chemically crosslinked starches and flours in these applications.

In some applications, the active ingredients are moisture sensitive. The thermally-inhibited starches and flours act as a moisture sink and protect the active ingredient by absorbing moisture.

DESCRIPTION OF THE PREFERRED EMBODIMENTS

All starches and flours are suitable for use herein. The thermally-inhibited starches and flours used herein are inert natural materials. More significantly, the thermally-inhibited starches and flours are substantially sterilized and, if stored and maintained properly, have a significantly reduced microbial content.

The thermally-inhibited starches and flours can be derived from any native source. A "native" starch or flour is one as it is found in nature in unmodified form. Typical sources for the starches and flours are cereals, tubers, roots, legumes and fruits. The native source can be corn, white corn, pea, potato, sweet potato, banana, barley, wheat, rice, sago, amaranth, tapioca, sorghum, waxy maize, waxy tapioca, waxy pea, waxy wheat, waxy rice, waxy barley, waxy potato, waxy sorghum, high amylose starches containing greater than 40% amylose, and the like. Preferred starches are potato, corn, rice, oat, tapioca, starches having an amylose content of 40% or greater, and waxy starches such as waxy maize, waxy tapioca, waxy rice, or waxy barley. The preferred flour is tapioca flour.

The thermal inhibition process may be carried out prior to or after other starch or flour reactions used to modify the starch or flour. The starches may be modified by conversion (i.e., acid-, enzyme-, and/or heat-conversion), oxidation, phosphorylation, etherification (e.g., by reaction with propylene oxide), esterification (e.g., by reaction with acetic anhydride or octenylsuccinic anhydride), and/or chemical crosslinking (e.g., by reaction with phosphorus oxychloride or sodium trimetaphosphate). The flours may be modified by bleaching or enzyme conversion. Procedures for modifying starches are described in the Chapter "Starch and Its Modification" by M. W. Rutenberg, pages 22–26 to 22–47, Handbook of Water Saluble Gums and Resins, R. L. Davidson, Editor (McGraw-Hill, Inc., New York, N.Y. 1980).

Native granular starches have a natural pH of about 5.0–6.5. When such starches are heated to temperatures above about 125° C. in the presence of water, acid hydrolysis (i.e., degradation) of the starch occurs. This degradation impedes or prevents inhibition. Therefore, the dehydration conditions need to be chosen so that degradation is minimized or avoided. Suitable conditions are thermally dehydrating at low temperatures and the starch's natural pH or thermally dehydrating at higher temperatures after increasing the pH of the starch to neutral or above. As used herein, "neutral" covers the range of pH values around pH 7 and is meant to include from about pH 6.5–7.5. A pH of at least 7 is preferred. More preferably, the pH is 7.5–10.5. The most preferred pH range is above 8 to below 10. At a pH above 12, gelatinization more easily occurs. Therefore, pH adjustments below 12 are more effective. It should be noted that the textural and viscosity benefits of the thermal inhibition process tend to be enhanced as the pH is increased, although higher pHs tend to increase browning of the starch or flour during the heat treating step.

To adjust the pH, the non-pregelatinized granular starch or flour is typically slurried in water or another aqueous medium, in a ratio of 1.5 to 2.0 parts of water to 1.0 part of starch or flour, and the pH is raised by the addition of any suitable base. Buffers, such as sodium phosphate, may be used to maintain the pH if needed. Alternatively, a solution of a base may be sprayed onto the powdered starch or flour until the starch or flour attains the desired pH, or an alkaline gas such as ammonia can be infused into the starch or flour. After the pH adjustment, the slurry is then either dewatered and dried, or dried directly, typically to a 2–15% moisture content. These drying procedures are to be distinguished from the thermal inhibition process steps in which the starch or flour is dehydrated to anhydrous or substantially anhydrous and then heat treated.

The starches or flours can be pregelatinized prior to or after the thermal inhibition process using methods known in the art. The amount of pregelatinization, and consequently, whether the starch will display a high or a low initial viscosity when dispersed in water, can be regulated by the pregelatinization procedure used, as is known in the art. The resulting pregelatinized starches are useful in applications where cold-water-soluble or cold-water-dispersible starches are used.

Pregelatinized granular starches and flours have retained their granular structure but lost their polarization crosses. They are pregelatinized in such a way that a majority of the starch granules are swollen, but remain intact. Exemplary processes for preparing pregelatinized granular starches are disclosed in U.S. Pat. No. 4,280,851 (issued Jul. 28, 1981 to E. Pitchon et al.), U.S. Pat. No. 4,465,702 (issued Aug. 14, 1984 to J. E. Eastman et al.), U.S. Pat. No. 5,037,929 (issued Aug. 6, 1991 to S. Rajagopalan), and U.S. Pat. No. 5,149,799 (issued Sept. 22, 1992 to Roger W. Rubens), the disclosures of which are incorporated by reference.

Pregelatinized non-granular have also lost their polarization crosses and have become so swollen that the starches have lost their granular structure and broken into fragments. They can be according to any of the known physical, chemical or thermal pregelatinization processes that destroy the granule such as drum drying, extrusion, or jet-cooking. See U.S. Pat. No. 1,516,512 (issued Nov. 25, 1924 to R. W. G. Stutzke); U.S. Pat. No. 1,901,109, (issued Mar. 14, 1933 to W. Maier); U.S. Pat. No. 2,314,459 (issued Mar. 23, 1943 to A. A. Salzburg; U.S. Pat. No. 2,582,198 (issued Jan. 8, 1957 to O. R. Ethridge); U.S. Pat. No. 2,805,966 (issued Sep. 10, 1957 to O. R. Ethridge); U.S. Pat. No. 2,919,214 (issued Dec. 29, 1959 to O. R. Ethridge); U.S. Pat. No. 2,940,876 (issued Jun. 14, 1960 to N. E. Elsas); U.S. Pat. No. 3,086,890 (issued Apr. 23, 1963 to A. Sarko et al.); U.S. Pat. No. 3,133,836 (issued May 19, 1964 to U. L. Winfrey); U.S. Pat. No. 3,137,592 (issued Jun. 16, 1964 to T. F. Pratzman et al.); U.S. Pat. No. 3,234,046 (issued Feb. 8, 1966 to G. R. Etchison); U.S. Pat. No. 3,607,394 (issued Sep. 21, 1971 to F. J. Germino); U.S. Pat. No. 3,630,775 (issued Dec. 18, 1971 to A. A. Winkler); and U.S. Pat. No. 5,131,953 (issued Jul. 21, 1992 to J. J. Kasica et al.); the disclosures of which are incorporated by reference.

If the pregelatinization process is performed first and the pregelatinized starch or flour is granular, the pH is adjusted by slurrying the pregelatinized granular starch or flour in water in a ratio of 1.5–2.0 parts to 1.0 part starch, and optionally, the pH is adjusted to neutral or greater. In another embodiment, the slurry is simultaneously pregelatinized and dried and the dried, starch or flour is thermally inhibited. If the thermal inhibition process is performed first, the starch or flour is slurried in water, the pH of the starch or flour is adjusted to neutral or greater, and the starch or flour is dried to about 2–15% moisture. The dried starch or flour is then dehydrated and heat treated. The inhibited starch or flour is reslurried in water, optionally pH adjusted, and simultaneously pregelatinized and dried.

For non-granular pregelatinized starches or flours prepared by drum drying, the pH is raised by slurrying the starch or flour in water at 30–40% solids and adding a sufficient amount of a solution of a base until the desired pH is reached.

For non-granular pregelatinized starches or flours prepared by the continuous coupled jet-cooking/spray-drying process of U.S. Pat. No. 5,131,953 or the dual atomization/spray-drying process of U.S. Pat. No. 4,280,851, the starch or flour is slurred at 6–10% solids in water and the pH is adjusted to the desired pH by adding a sufficient amount of a solution of a base until the desired pH is reached.

Suitable bases for use in the pH adjustment step include, but are not limited to, sodium hydroxide, sodium carbonate, tetrasodium pyrophosphate, ammonium orthophosphate, disodium orthophosphate, trisodium phosphate, calcium carbonate, calcium hydroxide, potassium carbonate, and potassium hydroxide, and any other bases approved for use under the applicable regulatory laws. The preferred base is sodium carbonate. It may be possible to use bases not approved provided they can be washed from the starch or flour so that the final product conforms to good manufacturing practices for the desired end use.

A thermal dehydration is carried out by heating the starch or flour in a heating device for a time and at temperature sufficient to reduce the moisture content to less than 1%, preferably 0%. Preferably, the temperatures used are 125° C. or less, more preferably 100°–120° C. The dehydrating temperature can be lower than 100° C., but a temperature of at least 100° C. will be more efficient for removing moisture.

Representative processes for carrying out a non-thermal dehydration include freeze drying or extracting the water from the starch or flour using a solvent, preferably a hydrophilic solvent, more preferably a hydrophilic solvent which forms an azeotropic mixture with water (e.g., ethanol).

For a laboratory scale dehydration with a solvent, the starch or flour (about 4–5% moisture) is placed in a Soxhlet thimble which is then placed in a Soxhlet apparatus. A suitable solvent is placed in the apparatus, heated to its reflux temperature, and refluxed for a time sufficient to dehydrate the starch or flour. Since during the refluxing the solvent is condensed onto the starch or flour, the starch or flour is exposed to a lower temperature than the solvent's boiling point. For example, during ethanol extraction the temperature of the starch is only about 40°–50° C. even though ethanol's boiling point is about 78° C. When ethanol is used as the solvent, the refluxing is continued for about 17 hours. The extracted starch or flour is removed from the thimble, spread out on a tray, and the excess solvent is allowed to flash off. The time required for ethanol to flash off is about 20–30 minutes. The dehydrated starch or flour is immediately placed in a suitable heating apparatus for the heat treatment. For a commercial scale dehydration any continuous extraction apparatus is suitable.

For dehydration by freeze drying, the starch or flour (4–5% moisture) is placed on a tray and put into a freeze dryer. A suitable bulk tray freeze dryer is available from FTS Systems of Stone Ridge, N.Y. under the trademark Dura-Tap. The freeze dryer is run through a programmed cycle to remove the moisture. The temperature is held constant at about 20° C. and a vacuum is drawn to about 50 milliTorr (mT). The starch or flour is removed from the freeze dryer and immediately placed into a suitable heating apparatus for the heat treatment.

After it is dehydrated, the starch or flour is heat treated for a time and at a temperature sufficient to inhibit the starch or flour. The temperature required will depend upon the starch base, with waxy starches requiring a higher temperature. The preferred heating temperatures are greater than about 100° C. For practical purposes, the upper limit of the heat treating temperature is about 200° C. Typical temperatures are 120°–180° C., preferably 140°–160° C., most preferably 160° C. The temperature selected will depend upon the amount of inhibition desired and the rate at which it is to be achieved.

The time at the final heating temperature will depend upon the level of inhibition desired. When a conventional oven is used, the time ranges from 1 to 20 hours, typically 2 to 5 hours, usually 3.5 to 4.5 hours. When a fluidized bed is used, the times range from 0 minutes to 20 hours, typically 0.5 to 3.0 hours. Longer times are required at lower temperatures to obtain more inhibited starches.

For most applications, the thermal dehydrating and heat treating steps will be continuous and accomplished by the application of heat to the starch or flour beginning from ambient temperature. The moisture will be driven off during the heating and the starch or flour will become anhydrous or substantially anhydrous. Usually, at the initial levels of inhibition, the peak viscosities are higher than the peak viscosities of starches or flours heated for longer times, although there will be greater breakdown in viscosity from the peak viscosity. With continued heat treating, the peak viscosities are lower, but the viscosity breakdowns are less.

The process may be carried out as part of a continuous process involving the extraction of the starch from a plant material.

As will be seen in the following examples, the source of the starch or flour, initial pH, dehydrating conditions, heating time and temperature, and equipment used are all interrelated variables that affect the amount of inhibition.

The heating steps may be performed at normal pressures, under vacuum or under pressure, and may be accomplished by conventional means known in the art. The preferred method is by the application of dry heat in dry air or in an inert gaseous environment.

The heat treating step can be carried out in the same apparatus in which the thermal dehydration occurs. Most conveniently, the process is continuous with the thermal dehydration and heat treating occurring in the same apparatus, as when a fluidized bed reactor is used.

The dehydrating and heat treating apparatus can be any industrial ovens, conventional ovens, microwave ovens, dextrinizers, dryers, mixers and blenders equipped with heating devices and other types of heaters, provided that the apparatus is fitted with a vent to the atmosphere so that moisture does not accumulate and precipitate onto the starch or flour. The preferred apparatus is a fluidized bed. Preferably, the apparatus is equipped with a means for removing water vapor, such as, a vacuum or a blower to sweep air or the fluidizing gas from the head-space of the fluidized bed. Suitable fluidizing gases are air and nitrogen. Dry air is preferred. For safety reasons, it is preferable to use a gas containing less than 12% oxygen.

Superior inhibited starches and flours having high viscosities with low percentage breakdown in viscosity are obtained in shorter times in the fluidized bed reactor than can be achieved using other conventional heating ovens or dryers.

Optional steps can be carried out to improve the color and/or flavor. They include washing the starch or flour with water and/or removing protein and/or lipid from the starch or flour prior to the dehydrating step and/or after the heat treating step. A bleaching agent (e.g., sodium chlorite) or an alkali can be used for the protein and/or lipid removal.

The starches may be inhibited individually or more than one may be inhibited at the same time. The starches may be inhibited in the presence of other materials or ingredients that would not interfere with the thermal inhibition process or alter the properties of the starch product.

Following the thermal inhibition step, the resulting starches may be screened to the desired particle size. If the starch is a non-pregelatinized granular starch, the starch can be slurried in water, washed, filtered, dried, and bleached. If the starch is a granular pregelatinized starch, the starch can be washed by any known methods that will maintain granular integrity.

If desired, the pH may be adjusted.

The thermally-inhibited starches and flours can be used wherever starches and flours are conventionally used in pharmaceutical products. They may be used in amounts ranging from <1% to up to 100%. Such uses are set out below.

Fillers and Carriers

Fillers and carriers act as diluents or bulking agents. Thermally-inhibited starches are particularly useful fillers for dry dosage capsules because of their improved flow characteristics.

Thermally-inhibited granular starches, preferably bleached, are useful as a carrier or diluent in tablets. Typically, corn, potato, and tapioca starches are used because they are inexpensive and/or widely available.

Thermally-inhibited starches, particularly granular starches, are also useful as carriers in dry, powdered medications such as the germicide and healing composition described in U.S. Pat. No. 4,668,692 (issued May 26, 1987 to D. O. Noorlander et al.). Since the carrier is the major part of the medicament, the improved flow properties of the thermally-inhibited starches are advantageous.

In the above uses a lightly inhibited starch is desired. Low moisture, whitened products are most desirable as is the microbial benefit provided by the thermal inhibition.

Suitable lightly inhibited starches and flours include corn starch which is adjusted to pH 8.0–9.5 and thermally dehydrated and heat treated at 150°–160° C. for 0–90 minutes; potato starch which is adjusted to pH 8.0–9.5 and thermally dehydrated and heat treated at 150°–160° C. for 0–60 minutes; tapioca starch which is adjusted to pH 8.0–9.5 and thermally dehydrated and heat treated at 150°–160° C. for 0–60 minutes; waxy corn starch which is adjusted to pH 8–9.5 and thermally dehydrated and heat treated at 150°–160° C. for 0–60 minutes; and waxy rice flour which is adjusted to pH 9.5 and thermally dehydrated and heat treated at 140°–160° C. for 0–15 minutes.

Wet Granulation Binders

All thermally-inhibited starches and flours, whether non-pregelatinized or pregelatinized, are useful as wet granulation binders or wet spheronization binders. Processing equipment such as extruders or high speed-high shear mixer/granulators is used to mix pharmaceutical formulas with solutions of the binders. The binders function to glue the tablet ingredients together. The resulting granulates should be more uniform in size, shape, and density, thus making them more suitable for pharmaceutical preparations such as solid dosage forms or for dry powder applications. The binders are stable, non-reactive materials that are wetted (cooked granular starches or dispersed pregelatinized starches) and used by those skilled in the art according to the processing equipment and final product requirements. In addition, the binders may dually serve as carrier coatings to additionally form barriers to protect, for example, moisture-sensitive and oxidation-sensitive ingredients, or used as coatings for controlled release formulas, or used as enteric coatings.

A preferred modification for the thermally-inhibited starches and flours used as wet granulation binders is conversion. This allows for higher paste concentrations for ease of use and maximizes performance. The conversion can be carried out prior to or after the thermal inhibitions. For wet spheronization non-converted starches are preferred.

Suitable lightly inhibited starches include waxy maize starches which is adjusted to pH 8.0–9.5 and thermally dehydrated and heat treated at 150°–160° C. for 0–60 minutes; waxy rice flour which is adjusted to pH 9.5 and thermally dehydrated and heat treated at 140°–160° C. for 0–15 minutes; corn starch which is adjusted to pH 8.0–9.5 and thermally dehydrated and heat treated at 150°–160° C. for 0–90 minutes; tapioca starch which is adjusted to pH 8.0–9.5 and thermally dehydrated and heat treated at 150°–160° C. for 0–45 minutes, and potato starch which is adjusted to pH 8.0–9.5 and thermally dehydrated and heat treated at 150°–160° C. for 0–60 minutes.

Suitable moderately inhibited starches include waxy maize starch which is adjusted to pH 9.5 and thermally dehydrated and heat treated at 160° C. for 60–120 minutes; waxy rice flour which is adjusted to pH 9.5 and thermally dehydrated and heat treated at 160° C. for 15–30 minutes; tapioca starch which is adjusted to pH 9.5 and thermally dehydrated and heat treated at 160° C. for 45–90 minutes; and potato starch which is adjusted to pH 9.5 and thermally dehydrated and heat treated to 160° C. for 60–90 minutes.

Also suitable is a lightly inhibited, low viscosity converted starch which is adjusted to pH 8.0–9.5 and thermally dehydrated and heat treated at 150°–160° C. for 0–60 minutes.

Direct Compression Binders

When native starches are used in direct compression, the tablets formed may vary in weight and hardness due to poor filling of the tablet press during manufacture. This is especially true when the pharmaceutical powder contains a high level of native starch. Thermally-inhibited starches improved filling due to their improved flow properties and result in tablets having more uniform weight hardness.

For a direct compression binder, non-pregelatinized or pregelatinized granular starches which have a low level of thermal inhibition and which are bleached are preferred. Low moisture, good flow properties, and absence of microbiological organisms are advantageous.

Suitable starches include corn starch which is adjusted to pH 8.0–9.5 and thermally dehydrated and heat treated at 150°–160° C. for 0–90 minutes; potato starch which is adjusted to pH 8.0–9.5 and heat-treated at 150°–160° C. for 0–60 minutes; and tapioca starch which is adjusted to pH 8.0–9.5 and thermally dehydrated and heat treated at 150°–160° C. for 0–45 minutes. Also suitable is a waxy maize starch which is adjusted to pH 8.0–9.5 and thermally dehydrated and heat treated at 150°–160° C. for 0– 60 minutes. Bleaching before or after the thermal inhibition is optional.

Binders for Capsule Filling

Any thermally-inhibited granular starch, preferably bleached, is useful as a diluent for dry dosage capsule-filling operations, provided it can be gravity- or force-fed into the capsule. Since the thermally-inhibited starches have improved flow properties, low moisture, and the absence of microbiological organisms, they are particularly useful in the powder mix. For capsule filling operations which require the formation of a plug, a thermally-inhibited starch having the properties required for a direct compression binder is preferred. Low levels of thermal inhibition are preferred.

Moisture Sinks

The low moisture content of the thermally-inhibited starches and flours makes them useful as moisture sinks. Excess free water in pharmaceutical formulations is preferentially absorbed by the starch to protect the moisture-sensitive ingredients and to increase the storage stability of the pharmaceutical composition.

Suitable thermally-inhibited starches and flours include all granular and non-granular forms and all degrees of thermal inhibition. Low levels of thermal inhibition are preferred. Because of their improved flow properties and low microbiological content, the thermally-inhibited starches and flours are particularly useful as moisture sinks.

Coatings

The thermally-inhibited starches and flours are useful as coating agents, particularly where high speed-high shear mixing and/or processing is used, where extrusion processing is used, or where spray applications using fluid bed processing are used. The coating agent is used to form barriers or coats to protect moisture-sensitive ingredients or to protect against oxidation. The coating agent is also used for controlled release formulations or where enteric coatings are desired. Suitable starches have been discussed under wet-granulation and spheronization. Thermally-inhibited flours provide additional hydrophobic properties making their use for controlled release or enteric formulations particularly useful. For example, a waxy rice flour adjusted to pH 9.5 and dehydrated and heat treated at 160° C. for 1 to 4 hours is suitable.

When used as a coating for particulates (e.g., Vitamin A) in bead form or for time release beads, the thermally-inhibited starches act as a moisture barrier and protect moisture-sensitive ingredients, provide stability during processing, protect against oxidation, and are microbiologically sterile. Amylose-containing thermally-inhibited starches are preferred. For such uses, the level of thermal inhibition is dictated by the coating requirements, and it is reasonable to use any level of inhibition provided the desired functional properties are achieved.

Disintegrants

Disintegrants are used in tablets to help the tablet break apart and release the active ingredient when the tablet is placed in a fluid environment.

The thermally-inhibited starches are microbiologically sterile and possess controlled swelling which makes them advantageous in disintegrants, providing the materials do not become tacky and impede water penetration into the solid dosage forms.

If non-pregelatinized thermally-inhibited starches are used as disintegrants, they should be lightly or moderately inhibited. Suitable thermally-inhibited starches are discussed under Wet Granulation Binders. If pregelatinized granular or pregelatinized non-granular starches are used as disintegrants, they should be moderately to highly inhibited. If highly or very highly thermally-inhibited starches are used as disintegrants, the starches should contain hydrophilic groups such as carboxymethyl groups, starch phosphates, or starch sulfates. Suitable starches are adjusted to pH 8–9.5 and dehydrated and heat treated at 150°–160° C. for 0–180 minutes.

Dusting Powers

The more thermally-inhibited starches, preferably the non-pregelatinized starches, are useful as dusting powders, e.g., surgical dusting powders, because of their microbiological sterility and greater resistance to gelatinization. Surgical rubber gloves are sterilized before use by steam autoclaving and accordingly any dusting powder used on the gloves must withstand steam sterilization. To achieve the level of thermal inhibition required to prevent gelatinization of the starch during the steam sterilization, a highly inhibited starch is needed. A high amylose starch, preferably crosslinked prior to thermal inhibition, is particularly useful. Suitable starches include a crosslinked starch which is adjusted to pH 9.5 and dehydrated and heat treated at 160° C. for 1.5–3 hours, a non-crosslinked starch which is adjusted to pH 9.5 and dehydrated and heat treated at 160°–180° C. for 3–6 hours; and a flour which is adjusted to pH 9.5 and dehydrated and heat treated at 160° C. for 1–4 hours. For dusting powder applications not requiring sterilization by autoclaving, e.g., body powders, pregelatinized thermally-inhibited starches are also suitable.

Viscosifiers

Thermally-inhibited starches are useful as shear and pH stable viscosifiers for liquid medications such as cough syrups and parenteral injectables (e.g., for tube feeding) and as components of inhalant sprays. Chemically stabilized amylopectin-containing starches are preferred in granular or pregelatinized form. Suitable chemical modifications include derivatization with octenylsuccinic anhydride (for surface active properties) or treatment with propylene oxide or acetic anhydride (for stabilization); or treatment with multifunctional crosslinking reagents (for additional inhibition effects). The chemical derivatization is preferably carried out before the thermal inhibition. A suitable viscosifier-texturizer includes tapioca starch or waxy maize starch which is adjusted to pH 9.5 and dehydrated and heat treated at 160° for 30–90 minutes.

Liquid Medicaments

Thermally-inhibited starches are used in a liquid medicament base to suspend controlled release active ingredients (e.g., hydrocodone which is a semi-synthetic narcotic antitussive and analgesic) or uncoated active ingredients (e.g., chlorpheniramine, which is an antihistamine drug).

The thermally-inhibited starches, preferably pregelatinized unless a cooking step is included in the preparation of the suspensions, are typically used in amounts sufficient to act as a thickener and viscosity stabilizer, e.g., about 12 wt. % of the aqueous base. The starch in combination with the other conventional ingredients used in the aqueous base, e.g., dyes, flavor, propylene glycol, methyl and propyl parabene, xanthan gum, sugar, ascorbic acid, polysorbate 80, and/or high fructose corn syrup, should provide the rheology necessary to suspend the active ingredients throughout the liquid medicament.

Suppositories

Thermally-inhibited amylose-containing starches which form a solid gel when dispersed in aqueous solutions are suitable. The preferred starches are converted, pregelatinized starches from root or tuber sources which are adjusted to pH 8.0–9.5 and dehydrated and heat treated at 150°–160° C. for 0–60 minutes. These starches may also be lightly chemically crosslinked.

Sample Preparation

Unless indicated otherwise, all the starches and flours used were provided by National Starch and Chemical Company of Bridgewater, N.J.

The controls for the test samples were from the same native source as the test samples, were unmodified or modified in the same manner as the test samples, and were at the same pH unless otherwise indicated.

All starches and flours, both test and control samples, were prepared and tested individually.

The pH of the samples was raised by slurrying the starch or flour in water at 30–40% solids and adding a sufficient amount of a 5% sodium carbonate solution until the desired pH was reached.

Measurements of pH, either on samples before or after the thermal inhibition steps, were made on samples consisting of one part starch or flour to four parts water.

After the pH adjustments, if any, all non-pregelatinized granular samples were spray-dried or flash-dried as conventional in the art (without gelatinization) to about 2–15% moisture.

After the pH adjustment, if any, slurries of the starches to be pregelatinized to granular pregelatinized starches were introduced into a pilot spray dryer, Type 1-KA#4F, from APV Crepaco, Inc., Dryer Division, Attleboro Falls, Mass., using a spray nozzle, Type 1/2J, from Spraying Systems Company of Wheaton, Ill. The spray nozzle had the following configurations: fluid cap 251376, air cap 4691312. The low initial cold viscosity samples were sprayed at a steam:starch ratio of 3.5–4.5:1, and the high initial cold viscosity samples were sprayed at a steam:starch ratio of 5.5–6.5:1. Moisture content of all pregelatinized samples after spray drying and before the dehydration step in the thermal inhibition process was 4–10%.

For the samples pregelatinized by drum drying the pH was raised by slurrying the starch or flour in water at 30–40% solids and adding a sufficient amount of a 5% sodium carbonate solution until the desired pH was reached. A single steam-heated steel drum at about 142°–145° C. was used for the drum drying.

For the samples pregelatinized by the continuous coupled jet-cooking/spray-drying process of U.S. Pat. No. 5,131,953 or the dual atomization/spray-drying process of U.S. Pat. No. 4,280,851, the starch or flour was slurred at 6–10% solids in water and the pH was adjusted to the desired pH by adding a sufficient amount of 5% sodium carbonate solution until the desired pH was reached.

Except where a conventional oven or dextrinizer is specified, the test samples were dehydrated and heat treated in a fluidized bed reactor, model number FDR-100, manufactured by Procedyne Corporation of New Brunswick, N.J. The cross-sectional area of the fluidized bed reactor was 0.05 sq meter. The starting bed height was 0.3–0.8 meter, but usually 0.77 meter. The fluidizing gas was air except where otherwise indicated. When granular non-pregelatinized starches were being heat treated, the gas was used at a velocity of 5–15 meter/min. When pregelatinized granular starches were being heat treated, the gas was used at a velocity of 15–21 meter/min. The side walls of the reactor were heated with hot oil, and the fluidizing gas was heated with an electric heater. The samples were loaded into the reactor and then the fluidizing gas was introduced, or the samples were loaded while the fluidizing gas was being introduced. No difference was noted in the samples in the order of loading. Unless otherwise specified, the samples were brought from ambient temperature up to no more than 125° C. until the samples became anhydrous and were further heated to the specified heat treating temperatures. When the heating temperature was 160° C., the time to reach that temperature was less than three hours.

The moisture level of the samples at the final heating temperature was 0%, except where otherwise stated. Portions of the samples were removed and tested for inhibition at the temperatures and times indicated in the tables.

Unless specified otherwise, the samples were tested for inhibition using the following Brabender Procedures.

Brabender Procedure—Non-Pregelatinized Granular Starches

Unless other stated, the following Brabender procedure was used. All samples, except for corn, tapioca and waxy rice flour, were slurried in a sufficient amount of distilled water to give a 5% anhydrous solids starch slurry. Corn, tapioca, and waxy rice flour were slurried at 6.3% anhydrous solids. The pH was adjusted to pH 3.0 with a sodium citrate, citric acid buffer and the slurry was introduced into the sample cup of a Brabender VISCO/Amylo/GRAPH (manufactured by C. W. Brabender Instruments, Inc., Hackensack, N.J.) fitted with a 350 cm/gram cartridge. The VISCO/Amylo/GRAPH records the torque required to balance the viscosity that develops when a starch slurry is subjected to a programmed heating cycle. The record consists of a curve tracing the viscosity through the heating cycle in arbitrary units of measurement termed Brabender Units (BU).

The starch slurry is heated rapidly to 92° C. and held for 10 minutes. The peak viscosity and viscosity ten minutes after peak viscosity were recorded in Brabender Units (BU). The percentage breakdown in viscosity (±2%) was calculated according to the formula:

$$\% \text{ Breakdown} = \frac{\text{peak} - (\text{peak} + 10')}{\text{peak}} \times 100,$$

where "peak" is the peak viscosity in Brabender units, and "(peak+10')" is the viscosity in Brabender Units at ten minutes after peak viscosity. If no peak viscosity was reached, i.e., the data indicate a rising (ris.) curve or a flat curve, the viscosity at 92° C. and the viscosity at 30 minutes after attaining 92° C. were recorded.

Using data from the Brabender curves, inhibition was determined to be present if, when dispersed at 5% or 6.3% solids in water at 92°–95° C. and pH 3, during the Brabender heating cycle, the Brabender data showed (i) no or almost no viscosity, indicating the starch was so inhibited it did not gelatinize or strongly resisted gelatinization; (ii) a continuous rising viscosity with no peak viscosity, indicating the starch was highly inhibited and gelatinized to a limited extent; (iii) a lower peak viscosity and a lower percentage breakdown in viscosity from peak viscosity compared to a control, indicating a moderate level of inhibition; or (iv) a slight increase in peak viscosity and a lower percentage breakdown compared to a control, indicating a low level of inhibition.

Characterization Of Inhibition of Non-Pregelatinized Granular Starches By Brabender Curves Characterization of a thermally-inhibited starch is made more conclusively by reference to a measurement of its Brabender viscosity after it is dispersed in water and gelatinized.

For non-inhibited starches, the cooking cycle passes through the initiation of viscosity, usually at about 60°–70° C., the development of a peak viscosity in the range of 67°–95° C., and any breakdown in viscosity when the starch is held at an elevated temperature, usually 92°–95° C.

Inhibited starches will show a Brabender curve different from the curve of the same starch that has not been inhibited (hereinafter the control starch). At low levels of inhibition, an inhibited starch will attain a peak viscosity somewhat higher than the peak viscosity of the control, and there may be no decrease in percentage breakdown in viscosity compared to the control. As the amount of inhibition increases, the peak viscosity and the breakdown in viscosity decrease. At high levels of inhibition, the rate of gelatinization and swelling of the granules decreases, the peak viscosity disappears, and with prolonged cooking the Brabender trace becomes a rising curve indicating a slow continuing increase in viscosity. At very high levels of inhibition, starch granules no longer gelatinize, and the Brabender curve remains flat.

Brabender Procedure—Pregelatinized Granular and Non-Granular Starches

The pregelatinized thermally-inhibited starch to be tested was slurried in a sufficient amount of distilled water to give a 4.6% anhydrous solids starch slurry at pH 3 as follows: 132.75 g sucrose, 26.55 g starch, 10.8 g acetic acid, and 405.9 g water were mixed for three minutes in a standard home Mixmaster at setting #1. The slurry was then introduced to the sample cup of a Brabender VISCO/Amylo/GRAPH fitted with a 350 cm/gram cartridge and the viscosity measured as the slurry was heated to 30° C. and held for 10 minutes. The viscosity at 30° C. and 10 minutes after hold at 30° C. were recorded. The viscosity data at these temperatures are a measurement of the extent of pregelatinization. The higher the viscosity at 30° C., the grater the extent of granular swelling and hydration during the pregelatinization process.

Heating was continued to 95° C. and held at that temperature for 10 minutes.

The peak viscosity and viscosity 10 minutes after 95° C. were recorded in Brabender Units (BU). The percentage breakdown was calculated using the previous formula:

If no peak viscosity was reached, that is, the data indicated a rising curve or a flat curve, the viscosity at 95° C. and the viscosity at 10 minutes after attaining 95° C. were recorded.

Characterization of Inhibition of Pregelatinized Granular Starches by Brabender Curves As discussed above, characterization of a thermally-inhibited starch is made more conclusively by reference to a measurement of its viscosity after it is dispersed in water and gelatinized using the instrument described above.

For pregelatinized granular starches, the level of viscosity when dispersed in cold water will be dependent on the extent to which the starch was initially cooked out during the pregelatinization process. If the granules were not fully swollen and hydrated during pregelatinization, gelatinization will continue when the starch is dispersed in water and heated. Inhibition was determined by a measurement of the starch viscosity when the starch was dispersed at 4.6% solids in water at pH 3 and heated to 95° C.

When the pregelatinized granular starch had a high initial cold viscosity, meaning it was highly cooked out in the pregelatinization process, the resulting Brabender traces will be as follows: for a highly inhibited that the starch, the trace will be a flat curve, indicating that the starch is already very swollen and is so inhibited starch it is resisting any further gelatinization or the trace will be a rising curve, indicating that further gelatinization is occurring at a slow rate and to a limited extent; for a less inhibited starch, the trace will he a dropping curve, indicating that some of the granules are fragmenting, but the overall breakdown in viscosity will be lower than that for a non-inhibited control or the trace will show a second peak but the breakdown in viscosity will be lower than that for a non-inhibited control.

When the pregelatinized starch had a low initial cold viscosity, meaning it was not highly cooked out in the pregelatinization process and more cooking is needed to reach the initial peak viscosity, the resulting Brabender traces will be as follows: for a highly inhibited starch, the trace will be a rising curve, indicating that further gelatinization is occurring at a slow rate and to a limited extent; for a less inhibited starch, the trace will show a peak viscosity as gelatinization occurs and then a drop in viscosity, but with a lower percentage breakdown in viscosity than for a non-inhibited control.

If no peak viscosity was reached, that is, the data indicated a rising curve or a flat curve, the viscosity at 95° C. and the viscosity at 10 minutes after attaining 95° C. were recorded.

Characterization of Inhibition of Pregelatinized Non-Granular Starches of Brabender Curves The resulting Brabender traces will be as follows: for a highly inhibited starch the trace will be flat, indicating that the starch is so inhibited that it is resisting any further gelatinization or the trace will be a rising curve, indicating that further gelatinization is occurring at a slow rate and to a limited extent; for a less inhibited starch, the trace will show a dropping curve, but the overall breakdown in viscosity from the peak viscosity will be lower than that for a non-inhibited control.

Characterization of Inhibition by Cooks

A dry blend of 7 g of starch or flour (anhydrous basis) and 14 g of sugar were added to 91 ml of water in a Waring blender cup at low speed, then transferred to a cook-up beaker, allowed to stand for 10 minutes, and then evaluated for viscosity, color, clarity and texture.

Some of the granular non-pregelatinized starch samples were tested for pasting temperature and/or gelatinization temperature using the following procedures.

Rapid Visco Analyzer (RVA)

This test is used to determine the onset of gelatinization, i.e., the pasting temperature. The onset of gelatinization is indicated by an increase in the viscosity of the starch slurry as the starch granules begin to swell.

A 5 g starch sample (anhydrous basis) is placed in the analysis cup of a Model RVA-4 Analyzer and slurried in water at 20% solids. The total charge is 25 g. The cup is placed into the analyzer, rotated at 160 rpm, and heated from an initial temperature of 50° C. up to a final temperature of 80° C. at a rate of 3° C./minute. A plot is generated showing time, temperature, and viscosity in centipoises (cP). The pasting temperature is the temperature at which the viscosity reaches 500 cP. Both pasting temperature and pasting time are recorded.

Differential Scanning Calorimetry (DSC)

This test provides a quantitative measurement of the enthalapy ($\Delta H$) of the energy transformation that occurs during the gelatinization of the starch granule. The peak temperature and time required for gelatinization are recorded. A Perkin-Elmer DSC-4 differential scanning calorimeter with data station and large volume high pressure sample cells is used. The cells are prepared by weighing accurately 10 mg of starch (dry basis) and the appropriate amount of distilled water to approximately equal 40 mg of total water weight (moisture of starch and distilled water). The cells are then sealed and allowed to equilibrate overnight at 4° C. before being scanned at from 25°–150° C. at the rate of 10° C./minute. An empty cell is used as the blank.

Angle of Repose Determination

This test measure the flow properties of the starch or flour. A large sheet of heavy Kraft paper (about 6 ft. square) is secured to a flat, level surface with masking tape. Two rings (3 in. and 4 in. in diameter) are clamped onto a ring stand (6×9 in. base and 24 in. rod) in such a way that the base faces in the opposite direction from the rings. The small ring is placed above the larger ring. To keep the funnels stationary, 1 in. pieces of heavy walled vacuum tubing (¼ in. base by ³⁄₁₆ in. wall) are cut lengthwise through one wall and fitted equidistantly at 3 locations on each ring. A chemical funnel having a 100 mm top interior diameter (ID) (Kimax 58) is modified by removing the existing stem and annealing a 8 mm I.D. glass tubing 85 mm in length as the stem. The modified funnel is placed in the large ring and the height is adjusted so that the orifice of the funnel is 1±0.1 cm above the paper. A powder funnel having a 60 mm top I.D. and 13 mm stem I.D. (Kimax 29020-04) is placed in the small ring and the ring is lowered as far as possible, i.e., until the clamps meet. The small funnel should be centered above the large funnel with the orifice of the large funnel stem parallel to the paper. Approximately 50 g of the sample to be tested are slowly added to the powder funnel while gently placing the top of an index finger over the orifice of the large funnel so that any sample which overflows the powder funnel does not flow out of the large funnel. The finger is slowly removed from the orifice while taking care not to move the funnel and allow the sample to flow onto the paper. Flow will cease when the top of the pile reaches the orifice of the funnel stem. With a pencil, the circumference of the sample pile is traced as accurately as possible without disturbing the sample. The sample is removed and the radius of the pile is measured. Each sample is run in triplicate. The test is repeated if the funnel stem becomes clogged before the pile meets the funnel orifice or if the pile is disturbed in any way. The funnels are cleaned after each run.

The average radius of the sample pile is calculated and the angle of repose is determined using the following formula:

$$\text{Tangent (angle of repose)} = \frac{\text{height of funnel orifice}}{\text{average radius of pile}}$$

Horiba Wet Particle Size Determination

For determination of the Horiba wet particle size determination, the thermally-inhibited starches were analyzed, according to the instruction manual-version 1.81C, of the Horiba, Model #LA-900, Laser Scattering Particle Size Distribution Analyzer (Horiba Instrument Inc., Irvine, Calif. 92174). This determination requires that the sample be added under agitation to a cup which contains distilled or de-ionized water until a desired concentration is achieved. The software package then automatically initiates the analysis.

EXAMPLES

The following examples will more fully illustrate the embodiments of the invention. In the examples, all parts are given by weight and temperature are in degrees Celsius unless otherwise noted. The thermally inhibited starches and controls in the following examples were prepared as described above and are defined by textural characteristics or in relation to data taken from Brabender curves using the above described procedures. The thermally-inhibited starches and flours are referred to as "T-I" starches and flours. Unless otherwise specified, the thermally-inhibited starches and flours referred to a "granular" starches are non-pregelatinized granular starches and flours.

In the first three examples, the moisture indicated is the moisture of the starch before the dehydration and heat treating steps. As indicated above, as the starches were brought from ambient temperature up to the heating temperature, the starches became anhydrous or substantially anhydrous.

In the tables the abbreviations "sl", "mod", "v", "ris" and "N.D." stand for slight or slightly moderate or moderately, very, rising, and not determined.

Example 1

This example illustrates the preparation of the starches of this invention from a commercial granular waxy maize base starch by the heat treatment process of this invention.

Processing conditions and their effects on viscosity and texture of waxy maize starch are set forth in the Tables below.

To obtain a heat-stable, non-cohesive thickener, samples of granular starch were slurried in 1.5 parts of water, the pH of the slurry was adjusted with the addition of a 5% $Na_2CO_3$ solution and the slurry was agitated for 1 hour, then filtered, dried, and ground. The dry starch samples (150 g) were placed into an aluminum foil pan (4"×5"×1½") and heated in a conventional oven under the conditions described below. Brabender viscosity measurements demonstrated that the most heat-stable starches were obtained by heating at 160° C. and a pH of at least 8.0 for about 3.5 to 6.0 hours.

| | | Process Variables | | Cold Evaluation of | |
|---|---|---|---|---|---|
| | | Heating - 160° C. | | Gelatinized Samples[d,e] | |
| Waxy | | Moisture | Time | | |
| Maize[a] | pH | (%) | (hrs.) | Viscosity | Texture |
| 1 | 6.0 | 10.9 | 2 | heavy to v. heavy | cohesive |
| 2 | 6.0 | 10.9 | 4 | thin to mod. | — |
| 3 | 8.2 | 10.6 | 3.5 | heavy to v. heavy | cohesive, less than unmodified control |
| 4 | 8.2 | 10.6 | 4 | heavy to v. heavy | sl. to mod. cohesive |
| 5 | 8.2 | 10.6 | 4.5 | heavy | non-cohesive |
| 6 | 8.2 | 10.6 | 5.5 | heavy, thinnest | non-cohesive |
| 7 | 8.2 | 10.6 | 6 | mod. heavy | non-cohesive |
| unmodified[b] | — | — | — | v. heavy | cohesive |
| cross-linked control[c] | — | — | — | v. heavy | non-cohesive |

[a]All samples were commercial samples of granular waxy maize starch obtained from National Starch and Chemical Company, Bridgewater, New Jersey.

-continued

| | | Process Variables | | Cold Evaluation of | |
|---|---|---|---|---|---|
| | | Heating - 160° C. | | Gelatinized Samples[d,e] | |
| Waxy | | Moisture | Time | | |
| Maize[a] | pH | (%) | (hrs.) | Viscosity | Texture |

[b]The unmodified control was a commercial granular waxy maize starch obtained from National Starch and Chemical Company, Bridgewater, New Jersey.
[c]The modified control was a commercial cross-linked, (phosphorous oxychloride treated) granular waxy maize starch obtained from National Starch and Chemical Company, Bridgewater, New Jersey.
[d]Samples were cooked by slurrying 7.0 g of starch (at 12% moisture) in 91 mls water at neutral pHs and heating the starch slurry for 20 minutes in a boiling water bath.
[e]The cold evaluation was carried out at 25° C.

| | Brabender Evaluation | | | | |
|---|---|---|---|---|---|
| | | Process Variables | | Brabender Viscosity[b] (BU) | |
| Waxy Maize[a] | pH | Heating Temp. (°C.) | Time (hrs.) | Peak Viscosity | Viscosity at 95° C./20 mins. |
| 3 | 8.2 | 160 | 3.5 | 985 | 830 |
| 4 | 8.2 | 160 | 4.0 | 805 | 685 |
| 5 | 8.2 | 160 | 4.5 | 640 | 635 |
| 6 | 8.2 | 160 | 5.5 | 575 | 570 |
| Unmodified control | — | none | none | 1640 | 630 |
| 1 | 6.0 | 160 | 2.0 | 1055 | 560 |
| 2 | 6.0 | 160 | 4.0 | 140 | 80 |

[a]See prior table for a description of samples.
[b]In the Brabender procedure, a sample containing 5.4% anhydrous solids of starch dispersed in water was heated rapidly to 50° C., then the heat was increased by 1.5° C. per minute to 95° C., and held for 20 minutes.

Example 2

This example illustrates that a variety of granular starches may be processed by the method of this invention to provide a non-cohesive thickener with properties similar to chemically crosslinked starches.

Processing conditions and their effects on the viscosity and texture of waxy barley, tapioca, V.O. hybrid and waxy rice starches are set forth in the tables below.

| | | Process Variables | | Cold Evaluation of | |
|---|---|---|---|---|---|
| | | Heating - 160° C. | | Gelatinized Sample[b] | |
| Sample[a] | pH | Moisture (%) | Time (hrs.) | Viscosity/Texture | |
| Waxy Barley Starch | | | | | |
| 1 | 8.7 | 8.5 | 1.5 | heavy | cohesive |
| 2 | 8.7 | 8.5 | 2.5 | heavy | sl. mod. cohesive |
| 3 | 8.7 | 8.5 | 3.5 | mod. heavy to heavy | non-cohesive |
| 4 | 5.2 | 10.8 | 1.5 | thin | — |
| 5 | 5.2 | 10.8 | 2.5 | thin/thinnest | — |
| Waxy Barley Control Tapioca Starch | | | 0 | heavy | cohesive |
| 6 | 8.8 | 10.3 | 2 | heavy to v. heavy | cohesive |
| 7 | 8.8 | 10.3 | 3 | heavy to v. | cohesive/ |

-continued

| | | Process Variables | | Cold Evaluation of | |
|---|---|---|---|---|---|
| | | Heating - 160° C. | | | |
| Sample[a] | pH | Moisture (%) | Time (hrs.) | Gelatinized Sample[b] Viscosity/Texture | |
| 8 | 8.8 | 10.3 | 4 | heavy heavy to v. heavy | less than Sample 6 sl. cohesive to sl. lumpy |
| 9 | 8.8 | 10.3 | 5 | heavy | non-cohesive to lumpy |
| Tapioca Control | | | 0 | v. heavy | cohesive |
| 10 | 5.5 | 10.9 | 3 | mod. heavy | — |
| Waxy Rice Starch | | | | | |
| Waxy Rice Control | | | 0 | v. heavy | cohesive |
| 1 | 9.1 | 9.0 | 2 | v. heavy | cohesive |
| 2 | 9.1 | 9.0 | 3 | heavy | sl. cohesive |
| 3 | 9.1 | 9.0 | 4 | heavy | sl. cohesive |
| Waxy Barley Starch | | | | | |
| 4 | 9.1 | 9.0 | 5 | mod. heavy to heavy | non-cohesive |

[a]Tapioca starch samples were commercial granular starch obtained from National Starch and Chemical Company, Bridgewater, New Jersey. Waxy barley starch samples were commercial granular starch obtained from AlKo, Finland. Waxy rice starch samples were commercial granular starch obtained from Mitsubishi Corporation, Japan.
[b]Samples were cooked by slurring 7.5 g of starch at 12% moisture in 100 mls of water and heating the starch slurry for 20 minutes in a boiling water bath.

| | | Process Variables | | Cold Evaluation of | |
|---|---|---|---|---|---|
| | | Heating - 160° C. | | | |
| Sample[a] | pH | Moisture (%) | Time (hrs.) | Gelatinized Sample[b] Viscosity/Texture | |
| V.O. Hybrid Starch | | | | | |
| 1 | 8.7 | 10.5 | 2.0 | heavy | cohesive v. sl. less than control |
| 2 | 8.7 | 10.5 | 3.0 | heavy | sl. mod. cohesive |
| 3 | 8.7 | 10.5 | 4.0 | mod. heavy to heavy | smooth, very sl. cohesive |
| 4 | 8.7 | 10.5 | 5.0 | mod. heavy | smooth, short, non-cohesive |
| 5 | 8.7 | 10.5 | 6.0 | moderate | smooth, short, non-cohesive |
| V.O. Hybrid Control | 5.9 | 11.4 | 0 | heavy | cohesive |

[a]V.O. hybrid starch samples were granular starches obtained from National Starch and Chemical Company, Bridgewater, New Jersey.
[b]Samples were cooked by slurrying 7.5 g of starch at 12% moisture in 100 mls of water and heating the starch slurry for 20 minutes in a boiling water bath.

The viscosity and texture evaluation results show that a non-cohesive, heat-stable starch thickener may be prepared from waxy barley, V.O. hybrid, tapioca and waxy rice starches by the process of this invention. The amount of inhibition (non-cohesive, thickening character in cooked aqueous dispersion) increased with increasing time of heat treatment.

Example 3

This example illustrates the effects of temperature, the pH, and starch moisture content on the viscosity and texture of the treated starch.

Part A:

A waxy maize starch sample (100 g) containing 20.4% moisture was heated in an oven at 100° C. for 16 hours in a sealed glass jar. A second sample was heated for 4 hours and a third sample was heated for 7 hours under the same conditions. The product viscosity and texture were compared to a 12.1% moisture granular waxy maize starch control using the cook evaluation method of Example 1.

Results are shown below.

| | Effect of Process Moisture | | |
|---|---|---|---|
| | Process Variables[b] Heat Time | Cold Evaluation of Gelatinized Starch[c] | |
| Sample[a] | (hrs.) | Viscosity | Texture |
| 1. Test (20.4% $H_2O$) | 16 | heavy, sl. thinner than control | cohesive |
| 2. Control (12.1% $H_2O$) | 0 | heavy | cohesive |
| 3. Test (20.4% $H_2O$) | 4 | heavy | cohesive |
| 4. Control (12.1% $H_2O$) | 0 | heavy | cohesive |
| 5. Test (20.4% $H_2O$) | 7 | heavy | cohesive |
| 6. Control (12.1% $H_2O$) | 0 | heavy | cohesive |

[a]Samples were obtained from National Starch and Chemical Company, Bridgewater, New Jersey.
[b]Process was conducted at pH 5.2.
[c]See Example 2 for cook conditions.

The results demonstrate that moisture added during the process yields a product which is as cohesive and undesirable as a control starch which had not been heated.

Part B:

Samples (900 g) of a commercial granular waxy maize starch (obtained from National Starch and Chemical Company, Bridgewater, N.J.) were placed in a 10"×15"×0.75" aluminum tray and heated in an oven at 180° C. for 15, 30, 45 and 60 minutes. The pH of the starch was not adjusted and remained at about 5.2 during the heating process. Sample viscosity and texture were evaluated by the method of Example 1.

As shown in below, the pH 5.2 samples were characterized by an undesirable, cohesive texture similar to that of a waxy maize starch control which had not been heat treated.

| | Effect of Acidic Process pH | | |
|---|---|---|---|
| | Process Variables[a] Heating Time | Cold Evaluation of Gelatinized Starch[b] | |
| Sample | (minutes) | Viscosity | Texture |
| 1 | 15 | v. heavy | cohesive |
| 2 | 30 | v. heavy | cohesive |
| 3 | 45 | v. heavy | cohesive |

-continued

Effect of Acidic Process pH

| Sample | Process Variables[a] Heating Time (minutes) | Cold Evaluation of Gelatinized Starch[b] Viscosity | Texture |
|---|---|---|---|
| 4 | 60 | heavy/v. heavy | cohesive |
| control | 0 | v. heavy | cohesive |

[a]The pH was not adjusted from that of the native waxy maize starch (a pH = 5.2) and Samples 1–4 correspond to starch treated by the process of U.S. Pat. No. 4,303,451 (no pH adjustment).
[b]See Example 2 for cook conditions.

Thus, a combination of selected factors, including the pH, moisture content and the type of native starch, determine whether a desirable, non-cohesive, heat-stable starch thickener is produced by the process of this invention.

Example 4

This example shows carrying out the thermal inhibition in the fluidized bed previously described. The effects of temperature and time at the indicated temperature on the level of inhibition granular waxy maize starch at pH 9.5 are shown below.

| Heating Time and Temperature | Viscosity (B.U.) Peak | Peak + 10' | Breakdown (%) |
|---|---|---|---|
| Control (none) | 1135 | 730 | 64.3 |
| 110° C. for 22 hrs. | 1185 | 930 | 18.1 |
| 160° C. for 0 hr. | 1055 | 880 | 16.6 |
| 160° C. for 2 hrs. | 665 | 660 | 0.7 |
| 175° C. for 0 hr. | 850 | 755 | 11.2 |
| 180° C. for 0 hr. | 715 | 680 | 4.9 |
| 190° C. for 0 hr. | 555 | 550 | 0.9 |
| 200° C. for 0 hr. | ris. | — | — |
| 200° C. for 2 hrs. | none | — | — |

The data show that inhibited anhydrous or substantially anhydrous samples can be obtained at heat treating temperatures between 110° and 200° C., with more inhibition occurring at higher temperatures or when the heat treatment was carried out for longer times at lower temperatures. The starch samples heated at 200° C. were highly inhibited, as shown by the rising curve, or completely inhibited, as shown by the fact the starch did not gelatinize.

Example 5

Samples of a granular high amylose starch (Hylon V—50% amylose) at its natural pH and pH 9.5 were evaluated for the effect of the high amylose content on inhibition. The starches were thermally inhibited at 160° C. in the fluidized bed for the indicated time. Due to the high levels of amylose, it was necessary to use a pressurized Visco/amylo/Graph (C. W. Brabender, Hackensack, N.J.) to obtain Brabender curves. Samples were slurried at 10% starch solids, heated to 120° C., and held for 30 minutes.

The results are shown below:

| High Amylose Corn | Natural pH Viscosity (BU) | | | pH 9.5 Viscosity (BU) | | |
|---|---|---|---|---|---|---|
| | Peak | Peak 10' | Breakdown (%) | Peak | Peak 10' | Breakdown (%) |
| Control | 1180 | 525 | 55.5 | 1180 | 525 | 55.5 |
| T-I (0 min.) | 700 | 235 | 66 | | | |
| T-I (120 min.) | 282 | 25 | 91 | 290 | 225 | 22 |

The data show that inhibition was obtained only on the high pH sample.

Example 6

This example shows the preparation of pregelatinized granular thermally-inhibited waxy maize starches. The pregelatinization step was carried out prior to the thermal inhibition. The fluidized bed previously described was used.

Starch slurries (30–40% solids), pH adjusted to 6, 8, and 10, were pregelatinized in a pilot size spray drier, Type-1-KA#4F (available from APV Crepaco, Inc., Dryer Division of Attle Boro Falls, Mass.) equipped with a Type 1/2 J spray nozzle (available from Spraying Systems Company of Wheaton, Ill.). The spray nozzle had the following configuration: fluid cap, 251376, and air cap, 4691312.

The resulting high and low viscosity and pregelatinized granular starches were dehydrated and heat treated at the temperature and time indicated. The thermally-inhibited starches were evaluated for inhibition using the Brabender procedure previously described.

The results are shown below:

| Heat Treatment Conditions | Viscosity (B.U.) | | | | | |
|---|---|---|---|---|---|---|
| | 30° C. | 30° C. + 10 min | Peak | 95° C. | 95° C. + 10 min | Breakdown (%) |
| pH 6.0 - High Initial Viscosity | | | | | | |
| Control | 1280 | 960 | 960 | 170 | 90 | 91 |
| 160° C. for 0 min. | 700 | 980 | 700 | 610 | 370 | 47 |
| 160° C. for 30 min. | 600 | 910 | 720 | 690 | 370 | 49 |
| 160° C. for 90 min. | 450 | 780 | 915 | 740 | 400 | 56 |
| 160° C. for 150 min. | 360 | 590 | 925 | 800 | 500 | 46 |
| pH 6.0 - Low Initial Viscosity | | | | | | |
| Control | 230 | 250 | 750 | 340 | 100 | 87 |
| 160° C. for 30 min. | 100 | 130 | 600 | 370 | 210 | 65 |
| 160° C. for 60 min. | 100 | 140 | 730 | 500 | 260 | 64 |
| 160° C. for 120 min. | 100 | 130 | 630 | 430 | 260 | 59 |
| 160° C. for 180 min. | 90 | 120 | 550 | 390 | 240 | 56 |

-continued

| Heat Treatment Conditions | 30° C. | 30° C. + 10 min | Peak | 95° C. | 95° C. + 10 min | Breakdown (%) |
|---|---|---|---|---|---|---|
| pH 8.0 - High Initial Viscosity | | | | | | |
| Control | 1400 | 1020 | 1020 | 270 | 100 | 90 |
| 160° C. for 0 min. | 700 | 1060 | 1050 | 760 | 280 | 73 |
| 160° C. for 60 min. | 260 | 600 | 1340 | 1200 | 780 | 42 |
| 160° C. for 90 min. | 240 | 440 | 1280 | 1240 | 1000 | 22 |
| 160° C. for 120 min. | 280 | 420 | 1320 | 1320 | 1280 | — |
| 160° C. for 150 min. | 120 | 200 | 860 | 860 | 820 | 7 |
| 160° C. for 180 min. | 180 | 260 | 980 | 980 | 920 | 8 |
| pH 8.0 - Low Initial Viscosity | | | | | | |
| Control | 250 | 250 | 820 | 340 | 130 | 84 |
| 160° C. for 0 min. | 50 | 100 | 690 | 460 | 270 | 61 |
| 160° C. for 60 min. | 40 | 50 | 840 | 590 | 320 | 62 |
| 160° C. for 120 min. | 20 | 30 | 720 | 650 | 450 | 38 |
| 160° C. for 180 min. | 20 | 30 | 590 | 570 | 450 | 24 |
| pH 10 - High Initial Viscosity | | | | | | |
| Control | 1010 | 740 | 1010 | 300 | 160 | 84 |
| 140° C. for 0 min. | 550 | 850 | 1280 | 1080 | 750 | 41 |
| 150° C. for 0 min. | 270 | 420 | 1680 | 1680 | 1540 | 8 |
| 160° C. for 0 min. | 170 | 240 | — | 1180 | 1440 | ris. |
| 160° C. for 30 min. | 80 | 85 | — | 410 | 650 | ris. |
| 160° C. for 60 min. | 60 | 60 | — | 150 | 300 | ris. |
| 160° C. for 90 min. | 50 | 50 | — | 80 | 140 | ris. |
| 160° C. for 120 min. | 40 | 40 | — | 80 | 130 | ris. |
| 160° C. for 150 min. | 40 | 40 | — | 60 | 90 | ris. |
| 160° C. for 180 min. | 40 | 40 | — | 45 | 70 | ris. |
| pH 10 - Low Initial Viscosity | | | | | | |
| Control | 200 | 190 | 615 | 350 | 190 | 69 |
| 130° C. for 0 min. | 110 | 180 | 1500 | 880 | 530 | 65 |
| 150° C. for 0 min. | 50 | 80 | 1670 | 1540 | 1250 | 25 |
| 160° C. for 0 min. | 30 | 30 | — | 1040 | 1320 | ris. |
| 160° C. for 30 min. | 30 | 30 | — | 380 | 640 | ris. |
| 160° C. for 60 min. | 30 | 30 | — | 150 | 310 | ris. |
| 160° C. for 90 min. | 10 | 10 | — | 50 | 120 | ris. |

The results show that some thermal inhibition was attained in all the dehydrated and heat treated pregelatinized granular starches and that increasing the initial pH and the heat treatment time increased the level of inhibition. For the samples at pH 6.0, at 0 and 30 minutes, the recorded peak viscosity was actually a second peak observed the initial high peak viscosity began to breakdown. For some of the samples at pH 10, no peak viscosity was reached, indicating a highly inhibited starch.

Example 7

This example describes the preparation of thermally-inhibited pregelatinized granular starches from additional starch bases as well as a waxy maize starch. The granular starches were adjusted to the indicated pH, pregelatinized using the procedure previously described, and heat treated in an oven at 140° C. for the indicated time. The cook evaluation and Brabender results are shown below.

| Heat Treatment | | | |
|---|---|---|---|
| pH | Hours | Viscosity of Cook | Texture of Cook |
| Cook Evaluation - Waxy Maize | | | |
| 6 | 2 | mod. | sl. cohesive, smooth |
| 6 | 4 | mod. | sl. cohesive, smooth |
| 6 | 6 | mod. | v. sl. cohesive, smooth |
| 6 | 8 | mod. | v. sl. cohesive, smooth |
| 8 | 2 | mod. | cohesive, smooth |
| 8 | 4 | mod. to heavy | sl. cohesive, smooth |
| 8 | 6 | moderate | v. sl. cohesive, smooth |
| 8 | 8 | moderate | v. sl. cohesive, smooth |
| 10 | 2 | mod. | sl. cohesive, smooth |
| 10 | 4 | mod. to heavy | non-cohesive, short, smooth |
| 10 | 6 | mod. | non-cohesive, short, smooth |
| 10 | 8 | mod. | non-cohesive, short, smooth |
| Cook Evaluation - Tapioca | | | |
| 6 | 2 | mod. to heavy | v. cohesive, long |
| 6 | 4 | mod. to heavy | cohesive |
| 6 | 6 | mod. | sl. cohesive, smooth |
| 6 | 8 | mod. | non-cohesive, short, smooth |
| 8 | 2 | mod. to heavy | v. cohesive |
| 8 | 4 | mod. to heavy | cohesive |
| 8 | 6 | mod. to heavy | non-cohesive, short, smooth |
| 8 | 8 | mod. to heavy | non-cohesive, short, smooth |
| 10 | 2 | mod. to heavy | cohesive, long |
| 10 | 4 | mod. to heavy | v. sl. cohesive, smooth |

-continued

| | | | |
|---|---|---|---|
| 10 | 6 | mod. | non-cohesive, short, smooth |
| 10 | 8 | mod. to heavy | non-cohesive, short, smooth |

Cook Evaluation - Potato

| | | | |
|---|---|---|---|
| 6 | 2 | heavy to v. heavy | v. cohesive, long |
| 6 | 4 | heavy | cohesive |
| 6 | 6 | mod. to heavy | sl. cohesive |
| 6 | 8 | mod. to heavy | v. sl. cohesive |
| 8 | 2 | heavy to v. heavy | v. cohesive, long |
| 8 | 4 | v. heavy | sl. cohesive |
| 8 | 6 | heavy | non-cohesive, sl. set, smooth |
| 8 | 8 | mod. | non-cohesive, v. sl. set, smooth |
| 10 | 2 | heavy | v. cohesive |
| 10 | 4 | heavy to mod. | sl. cohesive, v. sl. set, smooth |
| 10 | 6 | heavy to mod. | non-cohesive, short, mod. set, smooth |
| 10 | 8 | heavy to mod. | non-cohesive, short, mod. set, smooth |

| Heat Treatment Conditions | Viscosity (BU) | | | | | |
|---|---|---|---|---|---|---|
| | 30° C. | 30° C. + 10' | Peak | 95° C. | 95° C. + 10' | Breakdown (%) |
| Brabender Results - Waxy Maize at pH 8 and 140° C. | | | | | | |
| 2 hrs | 400 | 1115 | 1115 | 515 | 515 | 60 |
| 6 hrs | 400 | 955 | 1120 | 1120 | 1023 | 38 |
| Brabender Results - Tapioca at pH 8 | | | | | | |
| 2 hrs | 1140 | 2685 | 2685 | 2685 | 880 | 78 |
| 6 hrs | 370 | 800 | 1110 | 1110 | 890 | |

The results show that thermally-inhibited pregelatinized granular starches can be prepared using other starch bases and that for non-cohesive starches longer times and/or higher pHs are required when an oven rather than a fluidized bed is used for the dehydration and heat treatment.

Example 8

This example shows the preparation of pregelatinized, non-granular starches which were pregelatinized by drum drying and then thermally inhibited.

Samples of waxy maize, tapioca and potato starches, at pH 6, 8, and 10, were pregelatinized by drum-drying. The samples were placed in a 140° C. oven, dehydrated to anhydrous, and heat treated at 140° C. for the indicated times.

The viscosity and textural characteristics of the thermally-inhibited starches are set out below.

| Heating Time (hr.) | Cook Viscosity | Cook Texture |
|---|---|---|
| T-I Waxy Maize - pH 6 | | |
| 2 | heavy | very cohesive, pulpy |
| 4 | heavy to very heavy | cohesive, pulpy |
| 6 | heavy | slightly cohesive, pulpy |
| 8 | moderate to heavy | very slightly cohesive, pulpy |
| T-I Waxy Maize - pH 8 | | |
| 2 | heavy | very cohesive, pulpy |
| 4 | heavy | slightly cohesive, pulpy |
| 6 | moderate to heavy | very slightly cohesive, pulpy |
| 8 | moderate to heavy | very slightly cohesive, pulpy |
| T-I Navy Maize - pH 10 | | |
| 2 | heavy | cohesive, pulpy |
| 4 | heavy to moderate | very slightly cohesive, pulpy |
| 6 | moderate | non-cohesive, short, pulpy |
| 8 | moderate | non-cohesive, short, pulpy |
| T-I Tapioca - pH 6 | | |
| 2 | very heavy | cohesive, pulpy |
| 4 | heavy to very heavy | slightly cohesive, pulpy |
| 6 | moderately heavy | slightly cohesive, pulpy |
| 8 | heavy | slightly cohesive, pulpy |
| T-I Tapioca - pH 8 | | |
| 2 | heavy to very heavy | very cohesive, pulpy |
| 4 | heavy | very cohesive, pulpy |
| 6 | N.D. | N.D. |
| 8 | heavy | very slightly cohesive, pulpy |
| T-I Tapioca - pH 10 | | |
| 2 | heavy | cohesive, pulpy |
| 4 | heavy to very heavy | slightly cohesive, pulpy |
| 6 | heavy | non-cohesive, short, pulpy |
| 8 | moderately heavy | non-cohesive, short, pulpy |
| T-I Potato pH 6 | | |
| 2 | heavy to very heavy | cohesive, pulpy |
| 4 | heavy | cohesive, pulpy |
| 6 | moderate to heavy | cohesive, pulpy |
| 8 | moderate to heavy | cohesive, pulpy |
| T-I Potato - pH 8 | | |
| 2 | heavy to very heavy | very cohesive, pulpy |
| 4 | very heavy | cohesive, pulpy |
| 6 | very heavy | cohesive, pulpy |
| 8 | very heavy | cohesive, pulpy |
| T-I Potato - pH 10 | | |
| 2 | heavy to very heavy | very cohesive, pulpy |
| 4 | very heavy | slight set, slightly chunky |
| 6 | heavy | slight set, slightly chunky |
| 8 | moderately heavy | moderate set, slightly chunky |

N.D. — not determined

Brabenders were run on some of the above thermally-inhibited starches. The results are shown below.

| | Viscosity (BU) | | | | | |
|---|---|---|---|---|---|---|
| Heating Time (hr.) | 30° C. | 30° C. + 10' | Peak | 95° C. | 95° C. + 10' | Breakdown (%) |
| T-I Waxy Maize (pH 8) | | | | | | |
| 2 | 665 | 3000 | 4620 | 1120 | 300 | 94 |
| 6 | 700 | 1640 | 2445 | 2440 | 1900 | 22 |
| T-I Tapioca (pH 8) | | | | | | |
| 2 | 1500 | 3170 | 3290 | 680 | 600 | 82 |
| 6 | 1180 | 1870 | 1873 | 780 | 600 | 68 |

The results show that longer heating times and/or higher pHs are required to prepare non-cohesive starches at 140° C. It is expected that heating at 160° C., preferably in a fluidized bed, will provide non-cohesive starches at pHs other than 10.

Example 9

This example shows the preparation of another pregelantinized non-granular which was jet-cooked, spray-dried, and then thermally inhibited.

A granular high amylose starch (50% amylose) was jet-cooked and spray-dried using the continuous coupled jet-cooking/spray-drying process described in U.S. Pat. No. 5,131,953 and then thermally inhibited for 8 hours at 140° C. The jet-cooking/spray-drying conditions used were as follows: slurry—pH 8.5–9.0; cook solids—10%; moyno setting—about 1.5; cooking temperature—about 145° C; excess steam—20%; boiler pressure—about 85 psi; back pressure—65 psi; spray-dryer—Niro dryer; inlet temperature—245° C.; outlet temperature—115° C.; atomizer—centrifugal wheel.

The pregelatinized non-granular starch was adjusted to pH 8.7 and dehydrated and heat treated for 8 hours in an oven at 140° C. The characteristics of the resulting thermally inhibited starches are set out below.

High Amylose-pH 8.7

| | Viscosity (BU) | | | | |
|---|---|---|---|---|---|
| | 30° C. | 30° C. + 10' | Peak | 95° C. | 95° C. + 10' | Breakdown (%) |
| Control | 200 | 195 | 245 | 245 | 130 | 47 |
| T-I | 350 | 240 | 420 | 410 | 335 | 20 |

The results show that even a high amylose starch can be inhibited. There was less breakdown for the thermally-inhibited starch and the overall viscosity was higher.

Example 10

This example shows that thermally-inhibited starches can be prepared by drum-drying the starches prior to thermal inhibition. The resulting pregelatinized non-granular thermally-inhibited waxy maize starches are compared with thermally-inhibited pregelatinized non-granular waxy maize starches prepared by the continuous coupled jet-cooking and spray-drying process used in Example 9 and the thermally-inhibited pregelatinized granular starches prepared by the dual atomization/spray drying process described in U.S. Pat. No. 4,280,251 (which was used in Example 6).

The conditions used for the oven dehydration and heat treatment were 8 hours at 140° C. The characterization of the resulting thermally-inhibited starches is shown below.

| | Viscosity (BU) | | | | | |
|---|---|---|---|---|---|---|
| | 30° C. | 30° C. + 10' | Peak | 95° C. | 95° C. + 10' | Breakdown (%) |
| Drum-Dried/T-I Waxy Maize-pH 8 | | | | | | |
| Control | 640 | 2770 | 3,530 | 1,690 | 1,550 | 56 |
| T-I | 700 | 1640 | 2,440 | 2,365 | 1,860 | 24 |
| Jet-Cooked/Spray-Dried/T-I Waxy Maize-pH 8 | | | | | | |
| Control | 60 | 90 | 100 | 41 | 30 | 70 |
| T-I | 485 | 1540 | 1,545 | 1,330 | 1,230 | 20 |
| Steam Atomized/Spray-Dried/T-I Waxy Maize-pH 8 | | | | | | |
| Control | 100 | 1010 | 1080 | 340 | 170 | 84 |
| T-I | 360 | 950 | 970 | 860 | 650 | 33 |

The results show that after 8 hours heat treatment at 140° C. all the starches showed much less breakdown. The results also show that a higher degree of inhibition along with a higher peak viscosity can be obtained if the starch granules are completely disrupted as by drum drying or jet cooking.

Example 11

This example shows that the starch can be dehydrated by ethanol (EtOH) extraction and then heat treated to thermally inhibit the starch.

A granular waxy maize starch was slurried in 1.5 parts water (based on the weight of the starch) and adjusted to pH 7 and 9.5 with 5% sodium carbonate, held for 30 minutes, filtered, and dried on a tray to a moisture content of about 5–6% moisture. The starch having the pH of 5.3 was the native starch which was not pH adjusted.

For the dehydration, the dried pH 5.3, pH 7.0, and pH 9.5 starches were each separated into two samples. One sample was dried on trays in a forced draft oven at 80° C. overnight to thermally dehydrate the starch to <1% (0%) moisture. The other sample was placed in a Soxhlet extractor and allowed to reflux overnight (about 17 hours) with anhydrous ethanol (boiling point 78.32° C.). The ethanol-extracted sample was placed on paper so that the excess alcohol could flash off which took about 30 minutes. The ethanol-extracted starch was a free flowing powder which was dry to the touch.

For the heat treatment, the oven-dehydrated starches and ethanol-extracted starches were placed on trays in a forced draft oven and heated for 3, 5, and 7 hours at 160° C.

The thermally-inhibited starches and the controls were evaluated using the Brabender procedure previously described.

| | | | Viscosity (BU) | | |
|---|---|---|---|---|---|
| | Dehydration Method | Heat Treatment | Peak | Peak +10' | Breakdown (%) |
| Waxy Maize-pH 5.3 | | | | | |
| Control | — | — | 1245 | 330 | 74 |
| Dehydrated | oven | — | 1290 | 350 | 73 |
| Dehydrated | ethanol | — | 1205 | 245 | 80 |
| T-I | oven | 160° C. for 5 hrs. | 95 | 45 | 53 |
| T-I | ethanol | 160° C. for 5 hrs. | 255 | 185 | 28 |
| T-I | oven | 160° C. for 7 hrs. | 60 | 35 | 42 |

-continued

| Starch Base | Dehydration Method | Heat Treatment | Viscosity (BU) Peak | Peak +10' | Breakdown (%) |
|---|---|---|---|---|---|
| T-I | ethanol | 160° C. for 7 hrs. | 165 | 10 | 36 |
| Waxy Maize-pH 7.0 | | | | | |
| Dehydrated | oven | — | 1240 | 380 | 69 |
| T-I | oven | 160° C. for 7 hrs. | 298 | 240 | 20 |
| T-I | ethanol | 160° C. for 7 hrs. | 400 | 310 | 23 |
| Waxy Maize-pH 9.5 | | | | | |
| Dehydrated | oven | — | 1250 | 400 | 68 |
| Dehydrated | ethanol | — | 1070 | 350 | 67 |
| T-I | ethanol | 160° C. for 3 hrs | 665 | 635 | 5 |
| T-I | oven | 160° C. for 3 hrs | 680 | 655 | 4 |
| T-I | oven | 160° C. for 5 hrs. | 245 | 460 | ris. |
| T-I | ethanol | 160° C. for 5 hrs. | 160 | 375 | ris. |
| T-I | oven | 160° C. for 7 hrs. | 110 | 295 | ris. |
| T-I | ethanol | 160° C. for 7 hrs. | 110 | 299 | ris. |

The results show that the starches can be dehydrated by ethanol extraction. The results also show that dehydration without the subsequent heat treatment did not inhibit the starch. The viscosity breakdown was not significantly different from that of the native waxy maize starch. Both of the thermally-inhibited pH 7 starches were higher in viscosity than the pH 5.3 (as is) thermally-inhibited starches. The starches which were thermally-inhibited at pH 9.5 were moderately highly inhibited or highly inhibited (rising curve).

Example 12

Granular tapioca, corn and waxy rice starches and waxy rice flour were adjusted to pH 9.5, dehydrated in an oven and by extraction with ethanol, and heat treated at 160° C. for the indicated time. They were evaluated for Brabender viscosity using the procedure previously described.

The Brabender results are shown below.

| Starch Base | Dehydration Method | Heat Treatment Time | Viscosity (BU) Peak | Peak +10' | Breakdown (%) |
|---|---|---|---|---|---|
| Tapioca | | | | | |
| Dehydrated | oven | — | 745 | 330 | 58 |
| Dehydrated | ethanol | — | 720 | 330 | 54 |
| T-I | oven | 5 hrs. | 270 | 260 | 3 |
| T-I | ethanol | 5 hrs. | 260 | 258 | 1 |
| T-I | oven | 7 hrs. | 110 | 155 | ris. |
| T-I | ethanol | 7 hrs. | 100 | 145 | ris. |
| Tapioca | | | | | |
| Corn | | | | | |
| Dehydrated | oven | — | 330 | 280 | 15 |
| Dehydrated | ethanol | — | 290 | 250 | 14 |
| T-I | oven | 5 hrs. | 10 | 80 | ris. |
| T-I | ethanol | 5 hrs. | 10 | 170 | ris. |
| T-I | oven | 7 hrs. | 10 | 65 | ris. |
| T-I | ethanol | 7 hrs. | 10 | 45 | ris. |
| Waxy Rice | | | | | |
| Dehydrated | oven | — | 1200 | 590 | 50.8 |
| Dehydrated | ethanol | — | 12155 | 450 | 61.0 |
| T-I | oven | 5 hrs. | 518 | 640 | ris. |
| T-I | oven | 7 hrs. | 265 | 458 | ris. |
| T-I | ethanol | 7 hrs. | 395 | 520 | ris. |
| Waxy Rice Flour | | | | | |
| Dehyrated | oven | — | 895 | 700 | 22 |
| Dehydrated | ethanol | — | 870 | 410 | 53 |
| T-I | oven | 5 hrs. | 38 | 73 | ris. |
| T-I | ethanol | 5 hrs. | 140 | 260 | ris. |
| T-I | oven | 7 hrs. | 10 | 16 | ris. |
| T-I | ethanol | 7 hrs. | 40 | 100 | ris. |

The results show that pH 9.5-adjusted, ethanol-extracted, heat-treated tapioca and corn starches had viscosity profiles generally similar to those of the same starches which were thermally inhibited using oven-dehydration. The starches which were heated for 7 hours were more inhibited than the starches which were heat-treated for 5 hours.

Example 13

This example compares ethanol-extracted granular waxy maize starches and oven-dehydrated waxy maize starches which were heat treated in an oven for 5 and 7 hours at 160° C. The starches were adjusted to pH 8.03 prior to the dehydration.

The Brabender results are shown below.

| Dehydration/ Heat Treatment | Viscosity (BU) Peak | Peak +10' | Breakdown (%) |
|---|---|---|---|
| Oven/None | 1160 | 360 | 69 |
| EtOH/None | 1120 | 370 | 67 |
| Oven/5 hrs. | 510 | 455 | 11 |
| EtOH/5 hrs. | 490 | 445 | 9 |
| Oven/7 hrs. | 430 | 395 | 8 |
| EtOH/7 hrs. | 360 | 330 | 8 |

The thermally-inhibited starches were slurried at 6.6% solids (anhydrous basis), pH adjusted to 6.0–6.5, and then cooked out in a boiling water bath for 20 minutes. The resulting cooks were allowed to cool and then evaluated for viscosity, texture, and color.

| Dehydration Method | Time at 160° C. | Viscosity | Texture | Color |
|---|---|---|---|---|
| Oven | None | heavy to very heavy | cohesive | slightly off-white |
| Ethanol | None | heavy to very heavy | cohesive | slightly off-white |
| Oven | 5 hours | moderately heavy to heavy | non-cohesive, smooth | slightly tan, darker* |
| Ethanol | 5 hours | moderately heavy to heavy | non-cohesive, smooth | slightly tan |
| Oven | 7 hours | moderately heavy to heavy | non-cohesive, smooth | moderately tan, darker* |
| Ethanol | 7 hours | moderately heavy to heavy | non-cohesive, smooth | moderately tan |

*Slightly darker than ethanol-dehydrated samples.

These Brabender results show that highly inhibited starches can be obtained by both thermal and non-thermal dehydration. The cook evaluation results show that there is a benefit for the ethanol-dehydrated, thermally-inhibited starches in terms of reduced color. As will be shown hereafter, there is also a flavor improvement with ethanol dehydration.

Example 14

A granular waxy maize starch was pH adjusted to pH 9.5 as previously described. The starch was then placed in a freeze dryer and dried for 3 days until it was anhydrous (0% moisture). The freeze-dried (FD) starch was heat treated for 6 and 8 hours at 160° C. in a forced draft oven. Brabender evaluations were run. The results are shown below:

| | | Viscosity (BU) | | |
|---|---|---|---|---|
| Base | Heat Treatment | Peak | Peak +10' | Breakdown (%) |
| Control | — | 1260 | 320 | 75% |
| F.D. | — | 1240 | 320 | 74% |
| T-I | 160° C. for 6 hrs. | 340 | 465 | rising curve |
| T-I | 160° C. for 8 hrs. | 285 | 325 | rising curve |

The results show that the starch can be dehydrated by freeze drying and that the subsequent heat treatment is necessary to inhibit the starch. The starches are highly inhibited as shown by their rising viscosity.

Example 15

This example shows that thermal inhibition reduced the gelatinization temperature of the granular waxy maize starches.

The gelatinization temperature of an untreated waxy maize, a thermally-inhibited (T-I) waxy maize (pH adjusted to 9.5 "as is" at pH 6.0), and chemically-crosslinked (X-linked) waxy maize starches (0.02%, 0.04%, and 0.06% phosphorus oxychloride) were determined by Differential Scanning Calorimetry. The starches were thermally dehydrated and heat treated at 160° C. in an oven for the indicated time and temperature.

The peak gelatinization temperature (Gel. Temp.) and enthalapy (ΔH) are shown below.

| Waxy Maize | Peak Gel. Temp. (°C.) | Enthalpy (cal/g) |
|---|---|---|
| Unmodified | 74 | 4.3 |
| T-I (pH 9.5/160° C. for 8.5 hrs) | 68 | 2.9 |
| T-I (pH 6/160° C. for 8 hrs) | 59 | 2.8 |
| X-linked (0.02% POCl$_3$) | 73 | 4.4 |
| X-linked (0.04% POCl$_3$) | 72 | 4.2 |
| X-linked (0.06% POCl$_3$) | 74 | 4.2 |

The results show that there was a significant reduction in peak gelatinization temperature of the inhibited starches. The chemically crosslinked (X-linked) starches are essentially identical to the unmodified waxy starch in peak gelatinization temperature (72°–74° C. vs. 74° C.) and enthalapy (4.2–4.4 vs 4.3 cal/g). The reduced gelatinization temperature suggests that the overall granular structure has been altered by the dehydration and heat treatment.

Example 16

This example shows that the thermal inhibition may begin as early as 110° (230° F.), that it is substantially noticeable at 160° C. (320° F.), and that the gelatinization is unchanged or reduced. Granular wavy maize starches were pH adjusted to 7.0 and 9.5 and dehydrated and heat treated using air having a Dew point below 9.4° C. (15° F.) in the fluidized bed previously described at the indicated temperature and time.

The Brabender and DSC results are shown below.

| | Waxy Maize (pH 7.0) | | |
|---|---|---|---|
| Dehydration | Brabender Viscosity (BU) | | |
| Heat Treatment Conditions | Peak | Peak +10' | Breakdown (%) |
| Control* | 1010 | 220 | 78.2 |
| 93° C. for 0 min. | 1010 | 220 | 78.2 |
| 116° C. for 0 min. | 1030 | 250 | 75.7 |
| 127° C. for 0 min. | 1050 | 260 | 75.2 |
| 149° C. for 0 min. | 1130 | 350 | 69.0 |
| 160° C. for 0 min. | 1010 | 590 | 41.6 |
| 160° C. for 10 min. | 980 | 630 | 35.7 |
| 160° C. for 20 min. | 910 | 610 | 33.0 |
| 160° C. for 80 min. | 750 | 510 | 32.0 |
| 160° C. for 90 min. | 735 | 510 | 30.6 |

*Not pH-adjusted.

| Dehydration/ Heat Treatment Conditions | Peak Gelatinization Temperature** | Enthalpy** (cal/g) |
|---|---|---|
| Control* | 73.07 | 4.43 |
| 93° C. for 0 min. | 71.79 | 4.01 |
| 116° C. for 0 min. | 70.70 | 4.18 |
| 127° C. for 0 min. | 70.66 | 4.07 |
| 149° C. for 0 min. | 70.07 | 3.92 |
| 160° C. for 0 min. | 69.50 | 4.08 |
| 160° C. for 10 min. | 71.20 | 4.17 |
| 160° C. for 20 min. | 68.87 | 4.32 |
| 160° C. for 80 min. | 67.84 | 4.35 |
| 160° C. for 90 min. | 67.29 | 4.38 |

| Dehydration/<br>Heat Treatment<br>Conditions | Peak<br>Gelatinization<br>Temperature** | Enthalpy** (cal/g) |
|---|---|---|

*Not pH-adjusted.
**Average of 2 readings.

| Waxy Maize (pH 9.5) | | | |
|---|---|---|---|
| Dehydration/Heat<br>Treatment | Brabender Viscosity (B.U.) | | |
| Conditions | Peak | Peak +10' | Breakdown (%) |
| Control (pH 9.5) | 1240 | 300 | 75.8 |
| 93° C. for 0 min. | 1200 | 300 | 75.0 |
| 104° C. for 0 min. | 1205 | 320 | 73.4 |
| 110° C. for 0 min. | 1260 | 400 | 68.3 |
| 121° C. for 0 min. | 1230 | 430 | 65.0 |
| 127° C. for 0 min. | 1255 | 420 | 66.5 |
| 138° C. for 0 min. | 1245 | 465 | 62.7 |
| 149° C. for 0 min. | 1300 | 490 | 62.3 |
| 160° C. for 0 min. | 1120 | 910 | 18.8 |
| 160° C. for 60 min. | 750 | 730 | 2.7 |
| 160° C. for 90 min. | 690 | 680 | 1.4 |

| Dehydration/<br>Heat Treatment<br>Conditions | Peak Gelatinization<br>Temperature*<br>(0° C.) | Enthalpy<br>(cal/g)* |
|---|---|---|
| Control (pH 9.5) | 74.82 | 4.05 |
| 127° C. for 0 min. | 74.84 | 4.17 |
| 160° C. for 0 min. | 73.04 | 4.50 |
| 160° C. for 60 min. | 71.84 | 4.60 |
| 160° C. for 90 min. | 70.86 | 4.26 |

*Average of 2 readings.

The DSC results show that at the onset of inhibition there was a slight reduction in the peak gelatinization temperature and that as the inhibition temperature and time increased there is a reduction in the peak gelatinization temperature.

Example 17

This example shows the correlation between the RVA pasting temperature and time and DSC peak gelatinization temperature and time and the reduction in Brabender viscosity breakdown for various starch bases and for waxy maize starches dehydrated by various methods including heating, ethanol (ETOH) extraction, and freeze. The base starches were unmodified. The comparative starches dehydrated by drying starches were all adjusted to pH 9.5 before dehydration. The ethanol-extraction and freeze-drying were pH adjusted but not heat treated. The starches were heat treated in an oven at 160° C. for the indicated time except for the starches chemically crosslinked with 0.12% sodium trimetaphosphate (STMP) which were heat treated at 160° C. for the indicated time in the fluidized bed.

The results are shown below.

| | DSC | | | | Viscosity | | |
|---|---|---|---|---|---|---|---|
| | Pasting | | Peak | | (BU) | | Break- |
| Starch | Temp.<br>(°C.) | Time<br>(min) | Temp.<br>(°C.) | Time<br>(min) | Peak | Peak<br>+10' | down<br>(%) |
| | Tapioca | | | | | | |
| Tapioca | 68.20 | 3.7 | 70.61 | 6.6 | 1595 | 440 | 72.41 |
| | Dehydrated Thermally/Heat Treated | | | | | | |
| T-I<br>(2 hrs.) | 66.65 | 3.4 | 68.31 | 6.3 | 1230 | 560 | 54.47 |
| T-I<br>(6 hrs.) | 64.20 | 2.9 | 65.41 | 6.0 | 355 | 335 | 5.63 |
| Potato | 61.05 | 2.3 | 62.67 | 5.8 | 1825 | 1010 | 44.66 |
| | Dehydrated Thermall/Heat Treated at 160° C. | | | | | | |
| T-I<br>(3 hrs.) | 60.25 | 2.1 | 61.41 | 5.6 | 995 | 810 | 18.59 |
| T-I<br>(6 hrs.) | 60.20 | 2.1 | 61.13 | 5.6 | ris. | ris. | ris. |
| Waxy<br>Maize | 70.95 | 4.3 | 73.86 | 6.9 | 1215 | 350 | 71.79 |
| | Dehydrated Thermally/Heat Treated at 160° C. | | | | | | |
| T-I<br>(8 hrs.) | 68.15 | 3.7 | 70.71 | 6.6 | 760 | 720 | 5.2 |
| | Ethanol Dehydrated/Heat Treated at 160° C. | | | | | | |
| Comparative | 70.95 | 4.3 | 74.23 | 6.9 | 1250 | 400 | 68.00 |
| T-I<br>(2 hrs.) | 65.00 | 3.1 | 71.81 | 6.7 | ris. | ris. | ris. |
| T-I<br>(7 hrs.) | 63.85 | 2.8 | 68.12 | 6.3 | ris. | ris. | ris. |
| | Dehydrated by Freeze Drying/Heat Treated at 160° C. | | | | | | |
| Comparative | 71.30 | 4.4 | 74.16 | 6.9 | 1240 | 320 | 74.19 |
| T-I 6<br>hrs.) | 69.50 | 4.0 | 66.09 | 6.1 | ris. | ris. | ris. |
| T-I 8<br>hrs.) | 66.75 | 3.5 | 64.64 | 6.0 | ris. | ris. | ris. |
| Cross-<br>linked<br>(Con-<br>trol) | 71.70 | N.D. | 74.33 | 6.9 | ris. | ris. | ris. |
| | Dehydrated Thermally/Heat Treated at 160° C.* | | | | | | |
| Cross-<br>linked<br>T-I<br>(30 min. | 69.10 | N.D. | 71.66 | 6.7 | ris. | ris. | ris. |
| Cross-<br>linked<br>T-I<br>(150<br>min. | 66.00 | N.D. | 67.14 | 6.2 | ris. | ris. | ris. |

*fluidized bed

The results show that heat treatment of thermally and non-thermally dehydrated starches reduced the pasting and peak gelatinization temperatures while at the same time inhibiting viscosity breakdown. Because the gelatinization temperature has been lowered by the heat treatment of the dehydrated starch, less time is required to reach the pasting and gelatinization temperatures. The more highly inhibited starches showed a lower pasting temperature and less breakdown in viscosity.

Example 18

This example describes a visual evaluation of the dry powder flow properties of granular waxy maize starches adjusted to pH 9.5 and thermally dehydrated and heat treated in the fluidized bed previously described.

The starches evaluated are shown below:

| No. | Heat Treatment Conditions |
|---|---|
| 1 | 160° C. for 30 min. |
| 2 | 160° C. for 60 min. |
| 3 | 160° C. for 180 min. |

Powder No. 1 distributed fairly evenly and the flow pattern was uniform. It was somewhat fluid and had some dynamic quality. Only a slight amount of air was entrapped in the body of the powder. Powder No. 2 distributed evenly and the flow pattern was uniform. The powder was fluid and had a dynamic quality. There was no air entrapment in the body of the powder. Powder No. 3 distributed evenly and the flow pattern was uniform. The powder was fluid, water-like, and had a dynamic quality. No air was entrapped in the body of the powder. The control starch powder clumped and had an irregular flow. It had a cake-like static quality. Air was entrapped in the body of the powder.

Example 19

This example measures the flow properties of thermally-inhibited waxy maize starches by determining the angle of repose which is an indication of performance with regard to mobility/flow. The starches were adjusted to pH 9.5 and thermally inhibited by dehydration and heat treatment in the fluidized bed previously described.

The results are shown below:

| Heat Treatment Conditions | Angle of Repose * |
|---|---|
| 160° C. for 30 min. | 24.17 |
| 160° C. for 60 min. | 26.75 |
| 160° C. for 180 min. | 23.60 |

* Average of 5 readings.

The thermally-inhibited starches had good flow properties. The control did not flow. A chemically crosslinked and derivatized waxy corn starch also did not flow. The funnels were completely blocked upon addition of the sample. This starch would not even flow through powder funnels with larger internal diameter orifices without constant tapping. Similar results, i.e., no flow, were observed with native corn starch.

Example 20

The following example shows the wet particle size of waxy maize starches adjusted to pH 9.5 and dehydrated and heat treated in the fluidized bed previously described.

| Starch | Heat Treatment Conditions | Wet Particle Size (microns) |
|---|---|---|
| Control | | 15.198 |
| T-I | 160° C. for 0 min. | 17.029 |
| T-I | 160° C. for 90 min. | 19.251 |
| T-I | 169° C. for 180 min. | 18.880 |

The result shows that the thermally-inhibited starches swell more than the uninhibited control. As the starch became more highly inhibited, the swelling was somewhat reduced but the starch was still more swollen than the control. This increased swelling indicates that the thermally-inhibited starches would be useful as tablet disintegrants.

Example 21

This example shows that the thermally-inhibited starches and flours are substantially sterilized by the dehydration heat treatment in the fuidized bed. This property is useful in all pharmaceutical applications.

The testing was done according to the methods described in The United States Pharmacopeia (USP 23), The National Formulary (NF 18) dated Jan. 1, 1995, which is the procedure described at pages 17–19 of Chapter 3 "Aerobic Plate Count" by J. T. Peeler and L. J. Maturin, F.D.A. Bacteriological Analytical Manual, 7th Edition A.D.A.C. International, Arlington, Va. (1992). The starches were tested for the presence of Coliform, Salmonella, yeast and molds, *Staphylococcus aureus, Escherichia coli*, and *Pseudomonas aeruginosa*. The total plate count (Colony Forming Units—CFU) at 32° C. was determined and any organisms were identified.

PART A

Thermally-Inhibited Waxy Rice Flour

The flour was adjusted to pH 9.5, heat treated under the conditions shown below, and stored for about 3 months in non-sterilized, covered glass containers.

The results are shown below.

| Heat Treatment | Plate Count (CFU) |
|---|---|
| None | 7500 |
| 160° C. for 0 min. | <10 |
| 160° C. for 60 min. | <10 |
| 160° C. for 120 min. | <10 |

PART B

Thermally-Inhibited Waxy Maize Starch

The starch was adjusted to pH 9.5, and thermally-inhibited under the conditions shown below, and stored for about 2 months in non-sterilized, covered glass containers. The thermally-inhibited starches and the control starch were microbiologically tested for their total plate count and the presence of organisms using the above procedure.

The results are shown below.

| | Plate Count (CFU) |
|---|---|
| None | 2000 |
| 160° C. for 60 min. | <10 |
| 160° C. for 60 min. sample | <10 |
| 160° C. for 120 min. sample) | <10 |

Coliform, Salmonella, yeast and molds, *Staphylococcus aureus, Escherichia Coli*, and *Pseudomonas aeruginosa* were not present. A reading of <10 CFU means there is essentially nothing measurable. The above results are particularly surprising, especially since the thermally-inhibited flours and starches were not handled using aseptic techniques. If stored and maintained under sterile conditions, these starches should be useful in products where microbiological considerations are of concern.

Example 22

This example shows that alcohol dehydration provides better tasting thermally-inhibited starches.

The test performed was a "Triangle Taste Test" which employs three coded samples, two identical and one different, presented simultaneously. None of the samples are identified as the standard. Control and experimental treatments were systematically varied so that each was presented in odd and identical sample positions an equal number of times. The judge determined which of the three samples differed from the other two. A forced choice was required. Statistical analysis was used to determine whether a significant difference between treatments existed. The probability of choosing the different or odd sample by chance alone was one-third. Once the odd sample was chosen the judges were asked why the samples were different and which they preferred.

The starches tested were waxy maize starches adjusted to pH 9.5 and heat treated for 7 hours at 140° C. One sample was dehydrated by ethanol extraction and the other sample was thermally dehydrated prior to the thermal inhibition step.

The thermally-inhibited granular starches were washed by slurring the granular starch with 1.5 parts water, mixing for 10 minutes on a stir plate, vacuum filtering the slurry, and washing the starch cake twice with 50 ml. of distilled water. Then sufficient water was added to bring the slurry solids to 3%, the pH was adjusted to 6.0–6.5, and the slurry was cooked 20 minutes in a boiling water bath, cooled to slightly above room temperature, and evaluated.

The judges were given 20 ml samples for tasting. They observed a significant difference between the oven-dehydrated and ethanol-dehydrated starches. Nine out of the twelve judges chose the one different sample. All nine of the judges who could determine the different sample preferred the sample that was ethanol-extracted. Attributes that were used to describe the ethanol-extracted sample included clean, not bitter, and smooth compared to the oven-dehydrated sample.

Example 23

This example shows that an alcohol extraction of a granular thermally-inhibited starch provides a better tasting starch.

A thermally-inhibited, granular waxy maize (adjusted to pH 9.5 and dehydrated and heat treated at 160° C. for 180 minutes in the fluidized bed previously described was placed in a Soxhlet extraction apparatus and allowed to reflux overnight (about 17 hrs) using ethanol as the solvent. The extracted starch was then laid on paper to allow excess ethanol to flash off. The resulting dry starch was washed by slurring the starch with 1.5 parts water, mixing for 10 minutes on a stir plate, vacuum filtering the slurry, and washing the starch cake twice with 1.5 parts distilled water. Then sufficient water was added to bring the slurry solids to 3%, the pH was adjusted to 6.0–6.5, and the slurry was cooked in a boiling water bath for 20 minutes. The cook was cooled to slightly above room temperature and evaluated. The thermally-inhibited, non-ethanol-extracted starch was used as the control.

The taste test performed was a "Paired-Preference Test". Two samples are presented, simultaneously or sequentially. The judge is requested to express a preference based on a specific attribute, here which sample is cleaner. Results are obtained in terms of relative frequencies of choice of the two samples as accumulated for all participants. Six of the eight trained judges identified the ethanol-extracted sample as having a blander, cleaner flavor with less aftertaste.

Example 24

This example shows the effect of protein removal on the flavor (i.e., taste and smell) of a thermally-inhibited waxy maize starch.

Prior to the thermal inhibition process, the protein was extracted as follows. The starch was slurried at W=1.5 (50 lbs starch to 75 lbs of water) and the pH was adjusted to 3–3.5 with sulfuric acid. Sodium chlorite was added to give 2% on the weight of the starch. The starch was steeped overnight at room temperature. The pH was raised to about 9.5 using a 3% sodium hydroxide solution. The pH adjusted starch was washed well prior to drying. The protein level of the starch was reduced to about 0.1%.

The protein-extracted starch and untreated starch were thermally dehydrated and heat treated at 160° C. in the fluidized bed previously described. The protein level of the thermally-inhibited waxy maize control (pH 9.5) was about 0.3%.

Using a one-sided, directional difference taste testing procedure, as described in "Sensory Evaluation Techniques" by M. Meilgaard et al., pp. 47–111 (CRC Press Inc., Boca Raton, Fla. 1987), the protein-reduced, thermally-inhibited waxy maize was compared to the thermally-inhibited waxy maize which had not been protein-reduced prior to heat treatment.

For the taste test, 3% starch cooks (samples heated at 100° C. for 15 minutes) were prepared and panelists were asked to select the sample which was "cleaner" in flavor. All tests were done in a sensory evaluation room under red lights in order to negate any color differences that may have been present between samples.

The results are shown below:

| Trial # | Number of Panelists | Number of Positive Responses* | Significance Level ($\alpha$ risk)** |
| --- | --- | --- | --- |
| 1 | 15 | 12 | 5% |
| 2 | 14 | 11 | 5% |

*The number indicates those respondents who selected the protein-reduced product as being cleaner in flavor.
**The $\alpha$ values were determined from a statistical table. An $\alpha$ risk of 5% indicates (with 95% confidence) that the samples are statistically different, i.e., that the protein-reduced product is cleaner than the control.

The results show that protein removal prior to the heat treatment helps to improve the flavor of the thermally-inhibited waxy maize starches.

Example 25

Waxy maize starches were reacted with 7% and 3% by weight propylene oxide, thermally inhibited at the naturally occurring pH and at pH 9.5, and evaluated for inhibition.

| Temp (°C.) | Time (min) | Viscosity (BU) | | | | Breakdown (%) |
| --- | --- | --- | --- | --- | --- | --- |
| | | Peak | Peak + 10' | 92° C. | 92° C. + 30' | |
| Waxy Maize (7% PO and Natural pH) | | | | | | |
| Control | | 1420 | 395 | — | — | 72 |
| 160 | 0 | 1030 | 380 | — | — | 63 |
| 160 | 30 | 800 | 530 | — | — | 34 |
| 160 | 60 | 685 | 430 | — | — | 37 |
| 160 | 90 | 635 | 340 | — | — | 46 |
| 160 | 120 | 620 | 340 | — | — | 45 |
| 160 | 150 | 565 | 300 | — | — | 47 |
| 160 | 180 | 540 | 280 | — | — | 48 |

Viscosity (BU)

| Temp (°C.) | Time (min) | Peak | Peak + 10' | 92° C. | 92° C. + 30' | Break-down (%) |
|---|---|---|---|---|---|---|
| \multicolumn{7}{l}{Waxy Maize (7% PO and pH 9.5)} |
| Control | | 1420 | 395 | — | — | 72 |
| 160 | 0 | 1360 | 960 | — | — | 29 |
| 160 | 30 | 1010 | 950 | — | — | 6 |
| 160 | 60 | 1030 | 930 | — | — | 10 |
| 160 | 90 | 910 | 890 | — | — | 2 |
| 160 | 120 | 843 | 830 | — | — | 2 |
| 160 | 180 | 800 | 792 | — | — | 1 |
| \multicolumn{7}{l}{Waxy Maize (3% PO and Natural pH)} |
| Control | | 1155 | 280 | — | — | 76 |
| 160 | 0 | 900 | 360 | — | — | 60 |
| 160 | 30 | 570 | 370 | — | — | 35 |
| 160 | 60 | 480 | 350 | — | — | 27 |
| 160 | 90 | 440 | 300 | — | — | 32 |
| 160 | 120 | 375 | 235 | — | — | 37 |
| 160 | 150 | 310 | 185 | — | — | 40 |
| 160 | 180 | 300 | 180 | — | — | 40 |
| \multicolumn{7}{l}{Waxy Maize (3% PO and pH 9.5)} |
| Control | | 1155 | 280 | — | — | 76 |
| 160 | 0 | 1220 | 960 | — | — | 21 |
| 160 | 30 | 1020 | 950 | — | — | 7 |
| 160 | 60 | 880 | 865 | — | — | 2 |
| 160 | 90 | — | — | 750 | 790 | ris. |
| 160 | 120 | — | — | 620 | 780 | ris. |
| 160 | 150 | — | — | 510 | 750 | ris. |
| 160 | 180 | — | — | 400 | 700 | ris. |

The data show that derivatized starches, in this case etherified starches, can be thermally inhibited by this process and that a higher inhibition can be achieved at higher pH.

Example 26

Waxy maize starches were reacted with 1% by weight acetic anhydride ($Ac_2O$) and thermally inhibited at the naturally occurring pH and at pH 8.5.

The results are shown below.

Viscosity (BU)

| Temp (°C.) | Time (min) | Peak | Peak + 10' | 92° C. | 92° C. + 30' | Break-down (%) |
|---|---|---|---|---|---|---|
| \multicolumn{7}{l}{Waxy Maize (1% $Ac_2O$ and Natural pH at 160° C.)} |
| Control | | 1480 | 490 | — | — | 67 |
| 160 | 0 | 1030 | 570 | — | — | 45 |
| 160 | 30 | 880 | 650 | — | — | 26 |
| 160 | 60 | 720 | 510 | — | — | 29 |
| 160 | 120 | 605 | 490 | — | — | 19 |
| 160 | 180 | 545 | 460 | — | — | 16 |
| \multicolumn{7}{l}{Waxy Maize (1% $Ac_2O$ and pH 8.5 at 160° C.)} |
| Control | | 1480 | 490 | — | — | 67 |
| 160 | 0 | 1170 | 560 | — | — | 52 |
| 160 | 30 | 970 | 725 | — | — | 25 |
| 160 | 60 | 875 | 600 | — | — | 31 |
| 160 | 120 | 690 | 490 | — | — | 29 |
| 160 | 180 | 585 | 545 | — | — | 7 |

The data show that derivatized starches, in this case esterified starches, can be inhibited to varying degrees and that higher inhibition can be obtained at higher pH.

Example 27

This example shows the preparation of potato starches modified with an amino-multicarboxylic acid (CEPA) reagent, i.e., 2-chloroethylaminodipropionic acid and their subsequent thermal-inhibition.

Overhead stirring was used throughout this reaction. Deionized water (150 ml) was added to a liter beaker and heated to 45° C. with an external constant temperature bath. A total of 30 g sodium sulfate (30% on starch) was dissolved in the water followed by the addition of 100 g of the potato starch. A solution of 3% aqueous sodium hydroxide (25 ml) was added slowly with good agitation to minimize starch swelling. A 25% aqueous solution of the CEPA reagent (32 ml) to give an 8% starch treatment (dry basis) was added simultaneously with a 3% aqueous sodium hydroxide solution (170 ml). The addition rates used kept the level of caustic high so that pH was about 11.0 to 11.5 during the reaction. The reaction was run at 42°–45° C. for 16 hours and then neutralized by adding 3N hydrochloric acid to adjust pH to about 6.5, followed by stirring for 30 minutes. The starch was then filtered and washed twice with 150 ml of water and allowed to air dry. Analysis of the starch for bound nitrogen showed 0.25% N (dry basis).

The starches were adjusted to pH 9.5 and heat treated at 100° C., 110° C., 120° C., 130° C. and 140° C. for 0 minutes using the fluidized bed previously described.

Example 28

This example shows the thermal inhibition of converted starches.

Samples of waxy maize and tapioca starch were slurried in 1.5 parts water. The slurries were placed in a 52° C. water bath, with agitation, and allowed to equilibrate for one hour. Concentrated hydrochloric acid was added at 0.8% on the weight of the samples. The samples were allowed to convert at 52° C. for one hour. The pH was then adjusted to 5.5 with sodium carbonate and then to pH 8.5 with sodium hydroxide. The samples were recovered by filtering and air drying (approximately 11% moisture). The starches in 50 g amounts were placed in an aluminum tray, covered and placed into a forced draft oven at 140° C. for 5.5 hours.

The starches were evaluated for inhibition. The results are shown below.

| | Waxy Maize Viscosity (BU) | | | Tapioca Viscosity (BU) | | |
|---|---|---|---|---|---|---|
| Starches | Peak | Peak + 10' | Break-down (%) | Peak | Peak + 10' | Break-down (%) |
| Unmodified | 1380 | 250 | 81.9 | 810 | 225 | 72.2 |
| Acid-converted | 640 | 110 | 82.3 | 432 | 115 | 73.4 |
| T-I Acid-converted | 805 | 728 | 9.6 | 495 | 350 | 29.3 |

The results show that converted starches can be thermally inhibited by this process.

Example 29

An acid-converted hydroxypropylated waxy maize starch (25 WF starch reacted with 2% propylene oxide) was adjusted to pH 9.5 and thermally inhibited using the fluidized bed previously described. Samples were taken at 110° C., 125° C., and 140° C., all for 0 minutes.

The thermally-inhibited starch samples were cooked in tap water at 88°–93° C. (190°–200° F.) bath temperature for 30–60 minutes to yield solutions having a Brookfield viscosity of approximately 3000 cps. The viscosity stability at room temperature was evaluated.

The results are shown below:

|  | Control* | 110° C. | 125° C. | 140° C. |
|---|---|---|---|---|
| Matter Fluidity | 25.0 | 25.5 | 20.6 | 21.8 |
| Solids (%) | 18 | 18 | 18 | 18 |
| Initial Viscosity (cps) | 3160 | 2550 | 2820 | 2800 |
| Viscosity after 24 hours (cps) | 3280 | — | — | 2640 |
| Viscosity after 7 days (cps) | 3020 | 2475 | 2730 | 2810 |
| Viscosity after 8 days (cps) | 3000 | 1980 | 2140 | 2940 |
| Viscosity after 9 days (cps) | 2850 | 1990 | 2230 | 2870 |
| Appearance | clear | clear | clear | yellow |

*Hydroxypropylated waxy maize not thermally-inhibited.

Example 30

A granular waxy maize starch (pH 8.7) which had been lightly crosslinked with 0.04% phosphorous oxychloride was thermally-inhibited. The granular starch was jet-cooked and spray-dried using the coupled continuous jet-cooking/spray-drying process and conditions described in Example 8. The spray-dried starch was oven dehydrated and heat treated for 8 hours at 140° C.

The Brabender results and viscosity and textural characteristics of the resulting thermally-inhibited starch are set out below.

| Brabender Evaluation | | | | | |
|---|---|---|---|---|---|
| | Viscosity (BU) | | | | Breakdown (%) |
| | 30° C. | 30° C. + 10' | Peak | 95° C. | 95° C. + 10' | |
| Control | 150 | 165 | 215 | 120 | 70 | 67 |
| T-I Starch | 840 | 1,085 | 1,110 | 1,090 | 1,085 | 1 |

| Cook Evaluation | | |
|---|---|---|
| | Viscosity of Cook | Texture of Cook |
| Control | thin to moderate | cohesive, pulpy |
| T-I Starch | very heavy | non-cohesive, very pulpy, short |

The results show that after the dehydration and heat treatment steps the crosslinked starch was very highly inhibited.

Example 31

This example illustrates the use of a thermally-inhibited unmodified starch as a carrier in a medicament.

A dry composition useful for treating dairy animals for mastitis is prepared by mixing 10–15% ascorbic acid, 7–10% allantoin, and 75–83% of a lightly inhibited granular corn starch, with the total being 100%. The corn starch is adjusted to pH 9.5, heated to 160° C. for 0 minutes to dehydrate and thermally-inhibited the starch, substantially reduce the microbial content, and improve the dry flow properties of the starch.

Example 32

This example shows the use of lightly inhibited pregelatinized starch as a wet granulation binder in a compressed ascorbic acid tablet.

A total of 7 parts of a pregelatinized non-granular waxy maize starch or a pregelatinized granular corn starch is adjusted to pH 9.5 and dehydrated and heat treated at 160° C. for about 15 minutes. It is charged to a stainless steel mixer. Then 93 parts of ascorbic acid, in the form of unground crystals (29 wt. % retained on a 200 mesh screen and 71 wt. % passed by a 200 mesh screen), are then added. The mixture is granulated using about 25 parts of distilled water. The wet granulate is passed through a Fitzpatrick mill, equipped with a No. 5 screen operating at low speed, with knives forward. The milled granulate is dried overnight at about (105° F.) and then passed through a Fitzpatrick mill, equipped with a No. 12 screen operating at medium speed, with knives forward. Then 98 parts of the granulate are added to a mixture of 2 parts of calcium stearate. A granulate with low mechanical friability is obtained. It is compressed at a tablet weight of 570 mg using a 15/32" flat-faced beveled edge, scored punch. The tablets should be comparable to compressed tablets prepared with conventional pregelatinized corn starches such as National 1551 and Colorcon starch 1500. The tablets should release the active ingredient more rapidly due to the inhibition of its starch.

Example 33

This example describes the use of a thermally-inhibited corn starch (adjusted to pH 9.0 and dehydrated and heat treated at 160° C. for 30 minutes) in a controlled release formulation containing aspirin.

Aspirin (4.375 kg, 40 mesh/inch crystal USP) and the thermally-inhibited corn starch (0.2255 kg) are deaggregated through a 40 mesh/inch screen into the bowl of a Hobart mixer. The dry powders are mixed for 5 minutes at speed 1. A cellulose acetate phthalate solution is added to the mixing powders over a 30 second period while mixing at speed 1 and then for 4 minutes at speed 2. The wet granulate is discharged onto stainless steel trays and air dried until it can be forced through a 20 mesh/inch screen. The screened granulate is further air dried to remove residual solvent. The granulates are weighed, blended by tumbling, and compressed on a conventional rotary tablet press (half-inch flat bevelled edge tooling) using sufficient pressure to produce tablets containing 650 mg aspirin and having a hardness of 8–10 $K_p$ (Schleuniger).

It is expected that the thermally-inhibited starch will act as a disintegrant and a moisture sink thus improving the storage stability and reducing hydrolysis of the aspirin over time.

Example 34

This example describes the use of thermally-inhibited corn starch or potato starch (pH 8–9.5/0–15 min. at 140°–160° C.) as a carrier in a capsule containing an active ingredient which is used in the treatment of liver complaints, fibrinolysis, ulcers and immunological diseases such as articular rheumatism asthma and nephritis.

A combination of 100 parts of 4-t-butyl-2-cyclohexenecarboxylic acid, 70 parts finely granulated lactose, 30 parts of the thermally-inhibited starch, and were mixed well and packed in No. 2 capsules in an amount of 100 mg/capsule. Because the thermally-inhibited starches have improved flow properties, capsule filling should be made easier.

These thermally-inhibited starches will also act as a moisture sink.

Example 35

This example describes the use of the thermally-inhibited starches in a bacteria-containing suppository for treating vaginitis (see U.S. Pat. No. 3,639,566).

The suppositories are gelatin capsules which contain (a) Doderlein bacteria adsorbed on a thermally-inhibited, sterilized potato starch or corn starch (pH 8–9.5/140°–160° C. for 0–15 min.) and (b) oestriol. Preferably, the formulations contain 100–150 mg starch/bacteria adsorbate (105–107 live cells/gl., 0.4–0.6 g oestriol, and 350–400 mg bacteria-free starch. The starch serves as an absolute and an energy source which ensures the relatively prolonged survival of the bacteria.

Example 36

This example describes the use of a pregelatinized, converted or unconverted thermally-inhibited starch (pH 8–9.5/ 0–15 min at 140°–160° C.) as a starch matrix for controlled release compositions. Suitable starch bases include potato, corn, rice, tapioca, rye, oat, wheat or waxy maize.

The drug, flavor, sweetener, and other conventional ingredients are dispersed in a solidified starch melt and then formulated as tablets, capsules, granules, syrups, suspensions, gels, implants, aerosols, transdermal patches, or injectable dosage forms.

Now that the preferred embodiments of the present invention have been described in detail, various modifications and improvements thereto will become readily apparent to those skilled in the art. Accordingly, the spirit and scope of the invention are to be limited only by the appended claims and foregoing specification.

What is claimed:

1. An improved pharmaceutical product containing a pharmaceutically-active ingredient and an effective amount of a thermally-inhibited starch or thermally-inhibited flour which starch or flour is prepared by thermally or non-thermally dehydrating the starch or flour to anhydrous or substantially anhydrous and heat-treating the anhydrous or substantially anhydrous starch or flour for a time for up to 20 hours at 120°–180° C., which temperature and time is sufficient to inhibit the starch or flour.

2. The pharmaceutical product of claim 1, wherein the thermally-inhibited starch or flour is a pregelatinized granular or non-granular starch or flour.

3. The pharmaceutical product of claim 1, wherein the thermally-inhibited starch or flour is substantially sterilized and is further characterized by an improved flowability in comparison to a non-thermally inhibited starch or flour.

4. The pharmaceutical product of claim 1, wherein the pH of the starch or flour is raised to neutral or greater prior to the dehydration.

5. The pharmaceutical product of claim 1, wherein the thermally-inhibited starch or flour is a cereal, a tuber, a root or a legume starch or flour.

6. The pharmaceutical product of claim 1, wherein the starch is selected from the group consisting of banana, corn, pea, potato, sweet potato, barley, wheat, rice, sago, amaranth, tapioca, sorghum, V.O. hybrid waxy maize, waxy tapioca, waxy sorghum, waxy rice, waxy barley, waxy potato, a starch containing greater than 40% amylose, and combinations thereof.

7. The pharmaceutical product of claim 6, wherein the starch is corn, waxy maize, potato, wheat, rice, tapioca starch, or high amylose starch.

8. The pharmaceutical product of claim 6, wherein the thermally-inhibited starch is a bleached starch, a derivatized starch, a crosslinked starch, a converted starch, a derivatized and converted starch, a derivatized and crosslinked starch, or a converted and crosslinked starch.

9. The pharmaceutical product of claim 1, wherein the thermally-inhibited starch acts a carrier or a diluent and has improved flow properties.

10. The pharmaceutical product of claim 1, wherein the thermally-inhibited starch acts as a wet granulation binder, a spheronisation binder, or a capsule filling binder.

11. The pharmaceutical product of claim 1, wherein the thermally-inhibited starch acts as a direct compression binder.

12. The pharmaceutical product of claim 1, wherein the active ingredient is moisture sensitive and wherein the thermally-inhibited starch acts as a moisture sink.

13. The pharmaceutical product of claim 1, wherein the thermally-inhibited starch acts as a disintegrant.

14. The pharmaceutical product of claim 1, which is a dusting powder and wherein the thermally-inhibited starch acts as adsorbent.

15. The pharmaceutical product of claim 1, which is a liquid medicament and wherein the thermally-inhibited starch acts as a viscosifier.

16. The pharmaceutical product of claim 15, wherein the liquid medicament is a parenteral injectable composition or an inhalant.

17. The pharmaceutical product of claim 1, which is a suppository and wherein the thermally-inhibited starch acts as a gelling agent.

18. The pharmaceutical product of claim 1, wherein an active ingredient is coated with an aqueous dispersion of the thermally-inhibited starch.

19. The pharmaceutical product of claim 1, wherein the thermally-inhibited starch, after dispersion in water, is characterized by its improved viscosity stability in comparison to the non-thermally-inhibited base starch.

20. The pharmaceutical product of claim 1, wherein the starch is selected from the group consisting of banana, corn, pea, potato, sweet potato, barley, wheat, rice, sago, amaranth, tapioca, sorghum, V.O. hybrid waxy maize, waxy tapioca, waxy sorghum, waxy rice, waxy barley, waxy potato, a starch containing greater than 40% amylose, and combinations thereof.

21. The pharmaceutical product of claim 19, wherein the starch is corn, waxy maize, potato, wheat, rice, tapioca starch, or high amylose starch.

22. The pharmaceutical product of claim 19, wherein the thermally-inhibited starch is a bleached starch, a derivatized starch, a crosslinked starch, a converted starch, a derivatized and converted starch, a derivatized and crosslinked starch, or a converted and crosslinked starch.

* * * * *